(12) United States Patent
Yu et al.

(10) Patent No.: US 12,419,712 B2
(45) Date of Patent: Sep. 23, 2025

(54) EMULATION OF ROBOTIC ARMS AND CONTROL THEREOF IN A VIRTUAL REALITY ENVIRONMENT

(71) Applicant: Verb Surgical Inc., Santa Clara, CA (US)

(72) Inventors: Haoran Yu, Menlo Park, CA (US); Pablo Eduardo Garcia Kilroy, Menlo Park, CA (US); Bernard Fai Kin Siu, San Jose, CA (US); Eric Mark Johnson, Sunnyvale, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/434,467

(22) Filed: Feb. 6, 2024

(65) Prior Publication Data
US 2024/0207001 A1 Jun. 27, 2024

Related U.S. Application Data

(63) Continuation of application No. 17/687,452, filed on Mar. 4, 2022, now Pat. No. 11,944,401, which is a (Continued)

(51) Int. Cl.
*A61B 34/00* (2016.01)
*A61B 34/10* (2016.01)
(Continued)

(52) U.S. Cl.
CPC .............. *A61B 34/70* (2016.02); *A61B 34/10* (2016.02); *A61B 34/25* (2016.02); (Continued)

(58) Field of Classification Search
CPC ......... A61B 34/70; A61B 34/10; A61B 34/25; A61B 2090/3983; A61B 2034/101; (Continued)

(56) References Cited

U.S. PATENT DOCUMENTS

| 7,317,955 B2 | 1/2008 | McGreevy |
| 8,100,133 B2 | 1/2012 | Mintz et al. |

(Continued)

FOREIGN PATENT DOCUMENTS

| CA | 2997965 A1 | 4/2017 |
| CN | 1481764 A | 3/2004 |

(Continued)

OTHER PUBLICATIONS

Almusawi, Ahmed R.J., et al., "Surgical Operation Simulation Based on Virtual Reality," Medical Technologies National Congress (TIPTEKNO), 2016, 4 pages.
(Continued)

*Primary Examiner* — Abby Y Lin
*Assistant Examiner* — Renee LaRose
(74) *Attorney, Agent, or Firm* — Aikin & Gallant, LLP

(57) ABSTRACT

A virtual reality system providing a virtual robotic surgical environment, and methods for using the virtual reality system, are described herein. Within the virtual reality system, various user modes enable different kinds of interactions between a user and the virtual robotic surgical environment. For example, one variation of a method for facilitating navigation of a virtual robotic surgical environment includes displaying a first-person perspective view of the virtual robotic surgical environment from a first vantage point, displaying a first window view of the virtual robotic surgical environment from a second vantage point and displaying a second window view of the virtual robotic surgical environment from a third vantage point. Additionally, in response to a user input associating the first and second window views, a trajectory between the second and third vantage points can be generated sequentially linking the first and second window views.

20 Claims, 24 Drawing Sheets

Related U.S. Application Data continuation of application No. 16/018,028, filed on Jun. 25, 2018, now Pat. No. 11,284,955.

(60) Provisional application No. 62/526,910, filed on Jun. 29, 2017.

(51) Int. Cl.
*A61B 34/30* (2016.01)
*A61B 90/00* (2016.01)
*G02B 27/01* (2006.01)
*G06T 19/00* (2011.01)

(52) U.S. Cl.
CPC ........ *G02B 27/0172* (2013.01); *G06T 19/006* (2013.01); *A61B 2034/101* (2016.02); *A61B 2034/102* (2016.02); *A61B 2034/107* (2016.02); *A61B 2034/256* (2016.02); *A61B 34/30* (2016.02); *A61B 2090/3983* (2016.02); *G02B 2027/0138* (2013.01)

(58) Field of Classification Search
CPC .............. A61B 34/30; A61B 2034/256; A61B 2034/102; A61B 2034/107; G02B 27/0172; G02B 2027/0138; G02B 2027/0187; G02B 2027/014; G02B 27/017; G06T 19/006
See application file for complete search history.

(56) References Cited

U.S. PATENT DOCUMENTS

| | | | |
|---|---|---|---|
| 8,527,094 | B2 | 9/2013 | Kumar et al. |
| 8,600,551 | B2 | 12/2013 | Itkowitz et al. |
| 8,831,782 | B2 | 9/2014 | Itkowitz |
| 10,314,559 | B2 | 6/2019 | Razzaque et al. |
| 10,610,303 | B2 | 4/2020 | Johnson et al. |
| 2003/0109780 | A1 | 6/2003 | Coste-Maniere et al. |
| 2004/0091845 | A1 | 5/2004 | Azerad et al. |
| 2005/0162383 | A1 | 7/2005 | Rosenberg |
| 2006/0178559 | A1 | 8/2006 | Kumar et al. |
| 2007/0275359 | A1 | 11/2007 | Rotnes et al. |
| 2007/0293734 | A1 | 12/2007 | Coste-Maniere et al. |
| 2008/0091066 | A1 | 4/2008 | Sholev |
| 2008/0234866 | A1 | 9/2008 | Kishi et al. |
| 2009/0088634 | A1 | 4/2009 | Zhao et al. |
| 2009/0192524 | A1 | 7/2009 | Itkowitz et al. |
| 2010/0234857 | A1 | 9/2010 | Itkowitz et al. |
| 2011/0118748 | A1 | 5/2011 | Itkowitz |
| 2012/0237095 | A1* | 9/2012 | Zhao ................... G06V 10/757 382/128 |
| 2013/0066335 | A1 | 3/2013 | Baerwinkel et al. |
| 2013/0245375 | A1 | 9/2013 | Dimaio et al. |
| 2014/0088941 | A1 | 3/2014 | Banerjee et al. |
| 2014/0251702 | A1 | 9/2014 | Berger et al. |
| 2014/0276952 | A1 | 9/2014 | Hourtash et al. |
| 2015/0025549 | A1 | 1/2015 | Kilroy et al. |
| 2015/0134113 | A1 | 5/2015 | Konietschke et al. |
| 2015/0243100 | A1 | 8/2015 | Abovitz et al. |
| 2016/0140875 | A1 | 5/2016 | Kumar et al. |
| 2016/0166345 | A1 | 6/2016 | Kumar et al. |
| 2016/0257000 | A1 | 9/2016 | Guerin et al. |
| 2016/0278870 | A1 | 9/2016 | Quaid et al. |
| 2016/0314710 | A1* | 10/2016 | Jarc ..................... G09B 23/285 |
| 2016/0314717 | A1 | 10/2016 | Grubbs |
| 2016/0324664 | A1 | 11/2016 | Piron et al. |
| 2016/0345929 | A1 | 12/2016 | Azizian et al. |
| 2017/0056101 | A1 | 3/2017 | Eubanks |
| 2017/0076016 | A1 | 3/2017 | Mir et al. |
| 2017/0319282 | A1 | 11/2017 | Jarc et al. |
| 2017/0367771 | A1 | 12/2017 | Tako et al. |
| 2018/0001472 | A1 | 1/2018 | Konidaris et al. |
| 2018/0168780 | A1 | 6/2018 | Kopelman et al. |
| 2019/0307510 | A1 | 10/2019 | Rotenberg et al. |
| 2020/0038124 | A1 | 2/2020 | Lin et al. |
| 2020/0253673 | A1 | 8/2020 | Azizian et al. |
| 2022/0415210 | A1 | 12/2022 | Jarc et al. |

FOREIGN PATENT DOCUMENTS

| | | |
|---|---|---|
| CN | 200979766 Y | 11/2007 |
| CN | 102665589 A | 9/2012 |
| CN | 102905642 A | 1/2013 |
| CN | 104915979 A | 9/2015 |
| CN | 106030683 A | 10/2016 |
| DE | 102008013495 A1 | 9/2009 |
| DE | 102012206350 A1 | 10/2013 |
| GB | 2302655 A | 1/1997 |
| JP | 2003-532144 A | 10/2003 |
| JP | 2008-228967 A | 10/2008 |
| JP | 2013-510671 A | 3/2013 |
| JP | 2016-101506 A | 6/2016 |
| JP | 2016-519585 A | 7/2016 |
| JP | 2017-510826 A | 4/2017 |
| WO | 96/10957 A1 | 4/1996 |
| WO | 2015/002744 A1 | 1/2015 |
| WO | 2015/095715 A1 | 6/2015 |
| WO | 2016/077531 A1 | 5/2016 |
| WO | 2017/083768 A1 | 5/2017 |
| WO | 2017/160651 A1 | 9/2017 |

OTHER PUBLICATIONS

Communication Pursuant to Article 94(3) EPC for European Application No. 18749903.3 mailed Feb. 17, 2022, 4 pages.
Communication Pursuant to Article 94(3) EPC for European Application No. 18749903.3 mailed Mar. 29, 2021, 6 pages.
Decision on Rejection for Chinese Application No. 201880043599.3 mailed Jun. 6, 2022, 22 pages.
Examination Report for Australian Application No. 2018292597 mailed Nov. 18, 2020, 4 pages.
Examination Report for Australian Application No. 2018294236 mailed Jun. 28, 2021, 5 pages.
Examination Report for Australian Application No. 2018294236 mailed Sep. 21, 2020, 5 pages.
Examiner's Decision of Refusal for Japanese Application No. 2019-567256 mailed Sep. 28, 2021, 13 pages.
Examiner's Report for Canadian Application No. 3,061,333 mailed Aug. 24, 2022, 5 pages.
Examiner's Report for Canadian Application No. 3,061,333 mailed Nov. 12, 2020, 4 pages.
Examiner's Report for Canadian Application No. 3,061,333 mailed Sep. 2, 2021, 4 pages.
Examiner's Report for Canadian Application No. 3,066,476 mailed Aug. 17, 2021, 3 pages.
Examiner's Report for Canadian Application No. 3066476 mailed Jan. 29, 2021, 4 pages.
Final Notice of Preliminary Rejection for Korean Application No. 10-2019-7038354 mailed Dec. 3, 2021, 16 pages.
Final Office Action for U.S. Appl. No. 16/018,019 dated Mar. 26, 2021, 26 pages.
Final Office Action for U.S. Appl. No. 16/018,028 mailed Aug. 18, 2021, 36 pages.
Final Office Action for U.S. Appl. No. 16/019,132 mailed Oct. 29, 2020, 29 pages.
First Office Action for Chinese Application No. 201880001376.0 mailed Nov. 25, 2022, 21 pages.
International Preliminary Report on Patentability for International Application No. PCT/US2018/039778 mailed Jan. 9, 2020, 8 pages.
International Preliminary Report on Patentability for International Application No. PCT/US2018/040138 mailed Jan. 9, 2020, 13 pages.
International Search Report and Opinion dated Dec. 3, 2018 for related PCT Appln. No. PCT/US2018/040138, filed Jun. 26, 2018; 16 Pages.
International Search Report and Written Opinion dated Oct. 1, 2018 for related PCT Appln. No. PCT/US2018/039778, filed Jun. 27, 2018; 13 Pages.

(56) References Cited

OTHER PUBLICATIONS

Non-Final Office Action for U.S. Appl. No. 16/018,019 mailed Nov. 10, 2020, 44 pages.
Non-Final Office Action for U.S. Appl. No. 16/018,028 mailed Dec. 30, 2020, 52 pages.
Non-Final Office Action for U.S. Appl. No. 17/221,300 mailed Jun. 8, 2022, 18 pages.
Non-Final Office Action for U.S. Appl. No. 17/547,0II mailed Dec. 5, 2022, 21 pages.
Notice of Allowance for U.S. Appl. No. 17/221,300 mailed Oct. 14, 2022, 10 pages.
Notice of Final Office Action for Korean Application No. 10-2019-7038174 mailed Jun. 22, 2021, 13 pages.
Notice of Final Rejection for Korean Application No. 10-2019-7038354 mailed Oct. 21, 2021, 8 pages.
Notice of Office Action for Korean Application No. 10-2019-7038354 mailed Apr. 12, 2021, 15 pages.
Notice of Reasons for Refusal for Japanese Application No. 2019-564997 mailed Jun. 22, 2021, 6 pages.
Notice of Reasons for Rejection for Japanese Application No. 2019-564997 mailed Jan. 6, 2021, 7 pages.
Notice of Reasons for Rejection for Japanese Application No. 2019-567256 mailed Dec. 22, 2020, 7 pages.
Office Action and Search Report for Chinese Application No. 201880043599.3 mailed Mar. 29, 2021, 28 pages.
Office Action for U.S. Appl. No. 16/019,132 mailed Jun. 11, 2020, 30 pages.
Office Action for U.S. Appl. No. 16/799,614 mailed Aug. 17, 2020, 6 pages.
Preliminary International Search Report and Opinion dated Oct. 12, 2018 for related PCT Appln. No. PCT/US2018/040138, filed Jun. 26, 2018; 13 Pages.
Preliminary Office Action for Brazilian Application No. BR112019025752-7 mailed Jun. 14, 2022, 5 pages.
Second Office Action and Search Report for Chinese Application No. 201880043599.3 mailed Dec. 21, 2021, 27 pages.

\* cited by examiner

| Data Structure | Exemplary Fields | Field Description |
|---|---|---|
| Arm | position | Coordinates of the arm's origin |
| | rotation | Quaternion representing the rotation of the arm's origin |
| | segments | Ordered list of segments belonging to this arm |
| | tool | State of tool attached to this arm |
| | touch_points | Collection of touchpoints available on this arm |
| Arm segment | index | Index of the segment in the arm |
| | joint_type | Number indicating type of joint that this segment uses (e.g., 0=fixed, 1=rotation, 2=translation) |
| | joint_position | Coordinates of the joint on the segment |
| | joint_value | Number representing the current state of the joint (e.g., angle of rotation, offset of translation) |
| Table | position | Coordinates of the table origin |
| | rotation | Quaternion representing the rotation of the table |
| | elevation | Number representing the elevation of the table |
| | lateral_tilt | Number representing the lateral tilt angle |
| Table adapter | arm_id | ID number of the arm associated with this table adapter |
| | position | Coordinates of the root of the table adapter |
| | rotation | Quaternion representing the rotation of the root of the table adapter |
| | segments | Ordered list of segments belonging to the table adapter |
| Cannula | diameter | Inner diameter of the cannula |
| | is_inserted | Boolean indicating whether the cannula is inserted into the patient |
| Tool | name | String representing model name of tool (e.g., including substring indicating tool type, such as camera, grasper, forceps, scissors, dissector, retractor, stapler, etc.) |
| | is_energized | Boolean indicating whether the tool is energized |
| | remaining_uses | Integer representing remaining uses of the tool (e.g., clips in a clip applier) |
| Touchpoint | is_active | Boolean indicating whether touchpoint is activated/touched |
| | segment_id | ID of arm segment that the touchpoint is associated with |

FIG. 4B

| Data Structure | Exemplary Fields | Field Description |
|---|---|---|
| User input system | mode | Integer representing current input modality (e.g., none, teleoperation, camera, etc.) |
| | handheld_controller_statuses | Collection (number) of handheld controllers |
| Handheld controller | is_active | Boolean indicating whether the input device is held by a user |
| | arm_ids | Collection of arm IDs that are associated with (Selected by) this handheld controller |
| | handedness | Integer representing the handedness of the handheld controller (e.g., 0=unknown, 1=left, 2=right) |
| | position | Coordinates of the handheld controller |
| | rotation | Quaternion representing the rotation of the handheld controller |
| Collision event | entity_id_1 | Unique ID of first entity involved in collision |
| | entity_id_2 | Unique ID of second entity involved in collision |
| | contact_position | If known, the coordinates of the collision |
| Procedure | name | Name of the procedure |
| Reference frame | type | Integer indicating the type of reference frame (e.g., 0=surgeon console, 1=control tower, 2=custom) |
| | scale | X,Y,Z scale modifier of the reference frame |
| Control system framework | arms | Collection (number) of arms |
| | cannulas | Collection (number) of cannulas |
| | collisions | Collection of 0 or more collision indicators |
| | procedure | Procedure definition |
| | reference_frames | Collection 1 or more reference frames |
| | table | The operating table |
| | user_input | State of the user input system |
| | version | String representing the version number of the kinematics system |

FIG. 4C

EMULATION OF ROBOTIC ARMS AND CONTROL THEREOF IN A VIRTUAL REALITY ENVIRONMENT

CROSS-REFERENCE AND RELATED APPLICATIONS

This application is a continuation of co-pending U.S. patent application Ser. No. 17/687,452, filed Mar. 4, 2022, which is a continuation of U.S. patent application Ser. No. 16/018,028, filed Jun. 25, 2018, now U.S. Pat. No. 11,284,955, issued Mar. 29, 2022, which claims the benefit of U.S. Provisional Patent Application No. 62/526,910, filed Jun. 29, 2017, which are hereby incorporated by reference in their entirety.

TECHNICAL FIELD

This invention relates generally to the field of robotic surgery, and more specifically to new and useful systems and methods for providing virtual robotic surgical environments.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical instruments (e.g., an end effector, at least one camera, etc.) through the incisions into the patient. The surgical procedures may then be performed using the introduced surgical instruments, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator. A robotic arm may, for example, support at its distal end various devices such as surgical end effectors, imaging devices, cannulae for providing access to the patient's body cavity and organs, etc.

Robotic surgical systems are generally complex systems performing complex procedures. Accordingly, a user (e.g., surgeons) generally may require significant training and experience to successfully operate a robotic surgical system. Such training and experience is advantageous to effectively plan the specifics of MIS procedures (e.g., determine optimal number, location, and orientation of robotic arms, determine optical number and location of incisions, determine optimal types and sizes of surgical instruments, determine order of actions in a procedure, etc.).

Additionally, the design process of robotic surgical systems may also be complicated. For example, improvements in hardware (e.g., robotic arms) are prototyped as physical embodiments and physically tested. Improvements in software (e.g., control algorithms for robotic arms) may also require physical embodiments. Such cyclical prototyping and testing is generally cumulatively expensive and time-consuming.

SUMMARY

Generally, a virtual reality system for providing a virtual robotic surgical environment may include a virtual reality processor (e.g., a processor in a computer implementing instructions stored in memory) for generating a virtual robotic surgical environment, a head-mounted display wearable by a user, and one or more handheld controllers manipulable by the user for interacting with the virtual robotic surgical environment. The virtual reality processor may, in some variations, be configured to generate a virtual robotic surgical environment based on at least one predetermined configuration file describing a virtual component (e.g., virtual robotic component) in the virtual environment. The head-mounted display may include an immersive display for displaying the virtual robotic surgical environment to the user (e.g., with a first-person perspective view of the virtual environment). In some variations, the virtual reality system may additionally or alternatively include an external display for displaying the virtual robotic surgical environment. The immersive display and the external display, if both are present, may be synchronized to show the same or similar content. The virtual reality system may be configured to generate a virtual robotic surgical environment within which a user may navigate around a virtual operating room and interact with virtual objects via the head-mounted display and/or handheld controllers. The virtual reality system (and variations thereof, as further described herein) may serve as a useful tool with respect to robotic surgery, in applications including but not limited to training, simulation, and/or collaboration among multiple persons.

In some variations, a virtual reality system may interface with a real or actual (non-virtual) operating room. The virtual reality system may enable visualization of a robotic surgical environment and may include a virtual reality processor configured to generate a virtual robotic surgical environment comprising at least one virtual robotic component, and at least one sensor in a robotic surgical environment. The sensor may be in communication with the virtual reality processor and configured to detect a status of a robotic component corresponding to the virtual robotic component. The virtual reality processor is configured to receive the detected status of the robotic component and modify the virtual robotic component based at least in part on the detected status such that the virtual robotic component mimics the robotic component.

For example, a user may monitor an actual robotic surgical procedure in a real operating room via a virtual reality system that interfaces with the real operating room (e.g., the user may interact with a virtual reality environment that is reflective of the conditions in the real operating room). Detected positions of robotic components during a surgical procedure may be compared with their expected positions as determined from surgical pre-planning in a virtual environment, such that deviations from the surgical plan may trigger a surgeon to perform adjustments to avoid collisions (e.g., change a pose of a robotic arm, etc.).

In some variations, the one or more sensors may be configured to detect characteristics or status of a robotic component such as position, orientation, speed, and/or velocity. As an illustrative example, the one or more sensors in the robotic surgical environment may be configured to detect position and/or orientation of a robotic component such as a robotic arm. The position and orientation of the robotic arm may be fed to the virtual reality processor, which moves or otherwise modifies a virtual robotic arm corresponding to the actual robotic arm. As such, a user viewing the virtual robotic surgical environment may visualize the adjusted virtual robotic arm. As another illustrative example, one or more sensors may be configured to detect a collision involving the robotic component in the robotic surgical environment, and the system may provide an alarm notifying the user of the occurrence of the collision.

Within the virtual reality system, various user modes enable different kinds of interactions between a user and the virtual robotic surgical environment. For example, one variation of a method for facilitating navigation of a virtual robotic surgical environment includes displaying a first-person perspective view of the virtual robotic surgical environment from a first vantage point within the virtual robotic surgical environment, displaying a first window view of the virtual robotic surgical environment from a second vantage point and displaying a second window view of the virtual robotic surgical environment from a third vantage point. The first and second window views may be displayed in respective regions of the displayed first-person perspective view. Additionally, the method may include, in response to a user input associating the first and second window views, sequentially linking the first and second window views to generate a trajectory between the second and third vantage points. Window views of the virtual robotic surgical environment may be displayed at different scale factors (e.g., "zoom" levels), and may offer views of the virtual environment from any suitable vantage point in the virtual environment, such as inside a virtual patient, overhead the virtual patient, etc.

In response to a user input indicating selection of a particular window view, the method may include displaying a new first-person perspective view of the virtual environment from the vantage point of the selected window view. In other words, the window views may, for example, operate as portals facilitating transportation between different vantage points within the virtual environment.

As another example of user interaction between a user and the virtual robotic surgical environment, one variation of a method for facilitating visualization of a virtual robotic surgical environment includes displaying a first-person perspective view of the virtual robotic surgical environment from a first vantage point within the virtual robotic surgical environment, receiving a user input indicating placement of a virtual camera at a second vantage point within the virtual robotic surgical environment different from the first vantage point, generating a virtual camera perspective view of the virtual robotic surgical environment from the second vantage point, and displaying the virtual camera perspective view in a region of the displayed first-person perspective view. The camera view may, for example, provide a supplemental view of the virtual environment to the user that enables the user to monitor various aspects of the environment simultaneously while still maintaining primary focus on a main, first-person perspective view. In some variations, the method may further include receiving a user input indicating a selection of a virtual camera type (e.g., movie camera configured to be placed outside a virtual patient, an endoscopic camera configured to be placed inside a virtual patient, a 360-degree camera, etc.) and displaying a virtual model of the selected virtual camera type at the second vantage point within the virtual robotic surgical environment. Other examples of user interactions with the virtual environment are described herein.

In another variation of a virtual reality system, the virtual reality system may simulate a robotic surgical environment in which a user may operate both a robotically-controlled surgical instrument using a handheld controller and a manual laparoscopic surgical instrument (e.g., adjacent a patient table, or "over the bed"). For example, a virtual reality system for simulating a robotic surgical environment may include a virtual reality controller configured to generate a virtual robotic surgical environment comprising at least one virtual robotic arm and at least one virtual manual laparoscopic tool, a first handheld device communicatively coupled to the virtual reality controller for manipulating the at least one virtual robotic arm in the virtual robotic surgical environment, and a second handheld device comprising a handheld portion and a tool feature representative of at least a portion of a manual laparoscopic tool, wherein the second handheld device is communicatively coupled to the virtual reality controller for manipulating the at least one virtual manual laparoscopic tool in the virtual robotic surgical environment. For example, in some variations, the tool feature may include a tool shaft and a shaft adapter for coupling the tool shaft to the handheld portion of the second handheld device (e.g., the shaft adapter may include fasteners). The second handheld device may be a functioning manual laparoscopic tool or a mock-up (e.g., facsimile or genericized version) of a manual laparoscopic tool, whose movements (e.g., in the tool feature) may be mapped by the virtual reality controller to correspond to movements of the virtual manual laparoscopic tool.

The second handheld device may be modular. For example, the tool feature may be removable from the handheld portion of the second handheld device, thereby enabling the second handheld device to function as a laparoscopic handheld device (for controlling a virtual manual laparoscopic tool) when the tool feature is attached to the handheld portion, as well as a non-laparoscopic handheld device (e.g., for controlling a robotically-controlled tool or robotic arm) when the tool feature is detached from the handheld portion. In some variations, the handheld portion of the second handheld device may be substantially similar to the first handheld device.

The handheld portion of the second handheld device may include an interactive feature, such as a trigger or button, which actuates a function of the virtual manual laparoscopic tool in response to engagement of the interactive feature by a user. For example, a trigger on the handheld portion of the second handheld device may be mapped to a virtual trigger on the virtual manual laparoscopic tool. As an illustrative example, in a variation in which the virtual manual laparoscopic tool is a virtual manual laparoscopic stapler, a trigger on the handheld portion may be mapped to firing a virtual staple in the virtual environment. Other aspects of the system may further approximate the virtual tool setup in the virtual environment. For example, the virtual reality system may further include a patient simulator (e.g., mock patient abdomen) including a cannula configured to receive at least a portion of the tool feature of the second handheld device, to thereby further simulate the user feel of a manual laparoscopic tool.

Generally, a computer-implemented method for operating a virtual robotic surgical environment may include generating a virtual robotic surgical environment using a client application, where the virtual robotic surgical environment includes at least one virtual robotic component, and passing information between two software applications in order to effect movements of the virtual robotic component. For example, in response to a user input to move the at least one virtual robotic component in the virtual robotic surgical environment, the method may include passing status information regarding the at least one virtual robotic component from the client application to a server application, generating an actuation command based on the user input and the status information using the server application, passing the actuation command from the server application to the client application, and moving the at least one virtual robotic component based on the actuation command. The client application and the server application may be run on a shared processor device, or on separate processor devices.

In some variations, passing status information and/or passing the actuation command may include invoking an application programming interface (API) to support communication between the client and server applications. The API may include one or more definitions of data structures for virtual robotic components and other virtual components in the virtual environment. For example, the API may include a plurality of data structures for a virtual robotic arm, a virtual robotic arm segment (e.g., link), a virtual patient table, a virtual cannula, and/or a virtual surgical instrument. As another example, the API may include a data structure for a virtual touchpoint for allowing manipulation of at least one virtual robotic component (e.g., virtual robotic arm) or other virtual component.

For example, the method may include passing status information regarding a virtual robotic arm, such as position and orientation (e.g., pose of the virtual robotic arm). The client application may pass such status information to the server application, whereupon the server application may generate an actuation command based on kinematics associated with the virtual robotic arm.

As described herein, there are various applications and uses for the virtual reality system. In one variation, the virtual reality system may be used to expedite the R&D cycle during development of a robotic surgical system, such as by allowing simulation of potential design without the time and significant expense of physical prototypes. For example, a method for designing a robotic surgical system may include generating a virtual model of a robotic surgical system, testing the virtual model of the robotic surgical system in a virtual operating room environment, modifying the virtual model of the robotic surgical system based on the testing, and generating a real model of the robotic surgical system based on the modified virtual model. Testing the virtual model may, for example, involve performing a virtual surgical procedure using a virtual robotic arm and a virtual surgical instrument supported by the virtual robotic arm, such as through the client application described herein. During a test, the system may detect one or more collision events involving the virtual robotic arm, which may, for example, trigger a modification to the virtual model (e.g., modifying the virtual robotic arm in link length, diameter, etc.) in response to the detected collision event. Further testing of the modified virtual model may then be performed, to thereby confirm whether the modification reduced the likelihood of the collision event occurring during the virtual surgical procedure. Accordingly, testing and modifying robotic surgical system designs in a virtual environment may be used to identify issues before testing physical prototypes of the designs.

In another variation, the virtual reality system may be used to test a control mode for a robotic surgical component. For example, a method for testing a control mode for a robotic surgical component may include generating a virtual robotic surgical environment, the virtual robotic surgical environment comprising at least one virtual robotic component corresponding to the robotic surgical component, emulating a control mode for the robotic surgical component in the virtual robotic surgical environment, and, in response to a user input to move the at least one virtual robotic component, moving the at least one virtual robotic component in accordance with the emulated control mode. In some variations, moving the virtual robotic component may include passing status information regarding the at least one virtual robotic component from a first application (e.g., virtual operating environment application) to a second application (e.g., kinematics application), generating an actuation command based on the status information and the emulated control mode, passing the actuation command from the second application to the first application, and moving the at least one virtual robotic component in the virtual robotic surgical environment based on the actuation command.

For example, the control mode to be tested may be a trajectory following control mode for a robotic arm. In trajectory following, movement of the robotic arm may be programmed then emulated using the virtual reality system. Accordingly, when the system is used to emulate a trajectory following control mode, the actuation command generated by a kinematics application may include generating an actuated command for each of a plurality of virtual joints in the virtual robotic arm. This set of actuated commands may be implemented by a virtual operating environment application to move the virtual robotic arm in the virtual environment, thereby allowing testing for collision, volume or workspace of movement, etc.

Other variations and examples of virtual reality systems, their user modes and interactions, and applications and uses of the virtual reality systems, are described in further detail herein.

BRIEF DESCRIPTION OF THE DRAWINGS

FIGS. 4B and 4C are tables summarizing exemplary data structures and fields for an application program interface for communication between the virtual reality environment application and the kinematics application.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Robotic Surgical System Overview

Figure 1A:
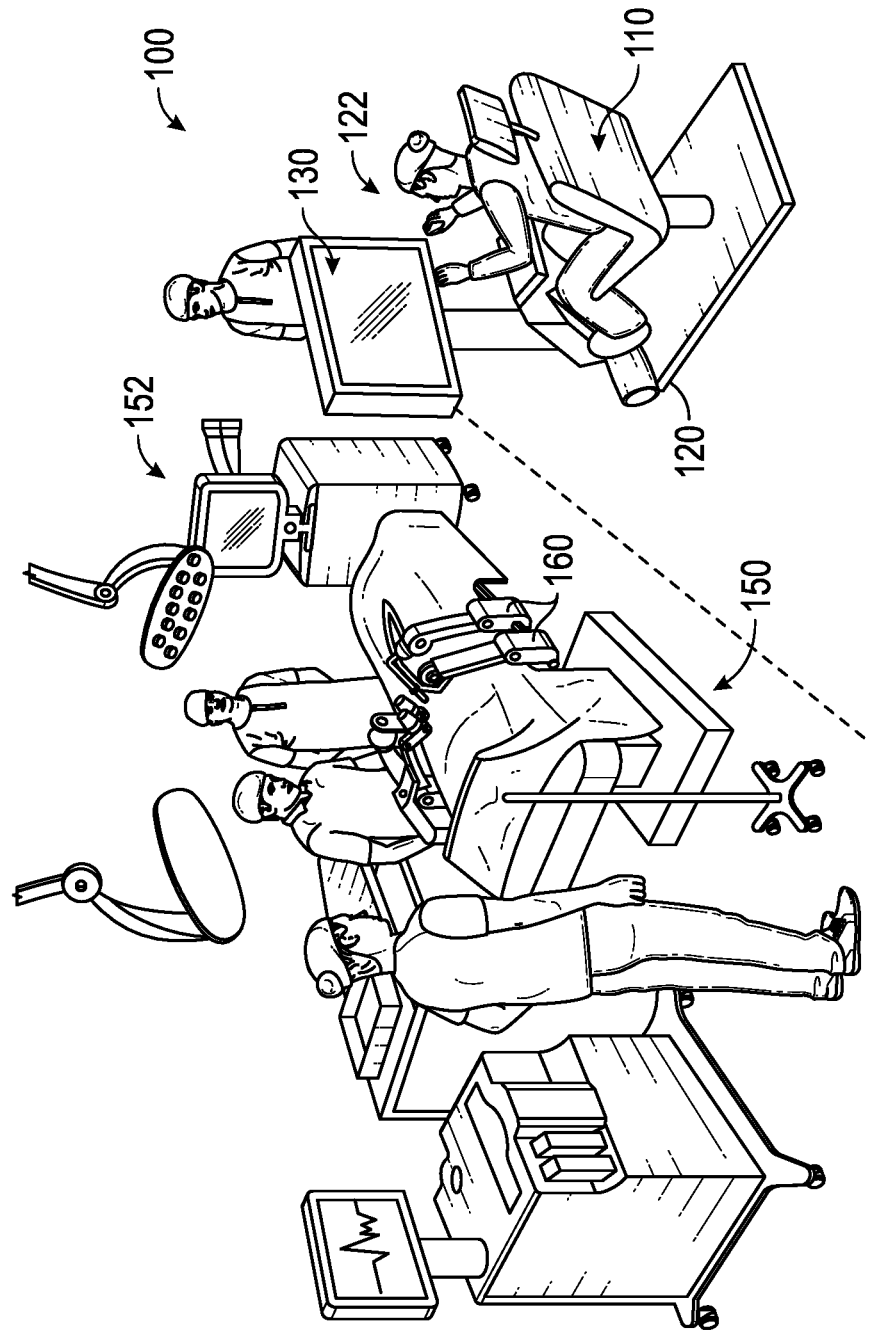
FIG. 1A depicts an example of an operating room arrangement with a robotic surgical system and a surgeon console.
Figure 1B:
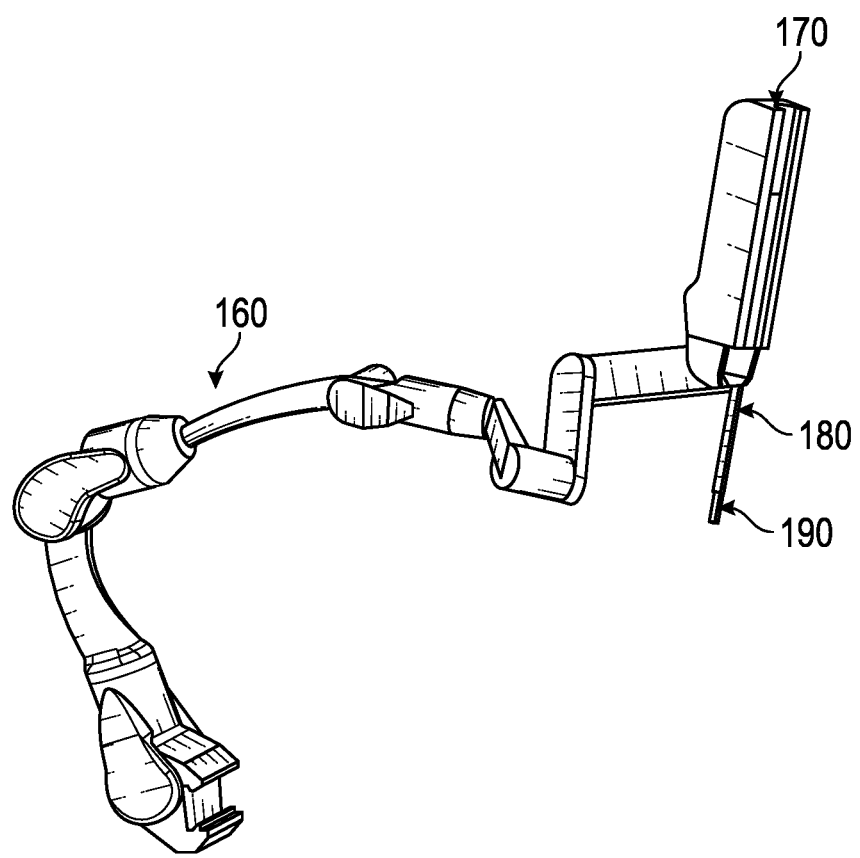
FIG. 1B is a schematic illustration of one exemplary variation of a robotic arm manipulator, tool driver, and cannula with a surgical tool.

An exemplary robotic surgical system and surgical environment is illustrated in FIG. 1A. As shown in FIG. 1A, a robotic surgical system 150 may include one or more robotic arms 160 located at a surgical platform (e.g., table, bed, etc.), where end effectors or surgical tools are attached to the distal ends of the robotic arms 160 for executing a surgical procedure. For example, a robotic surgical system 150 may include, as shown in the exemplary schematic of FIG. 1B, at least one robotic arm 160 coupled to a surgical platform, and a tool driver 170 generally attached to a distal end of the robotic arm 160. A cannula 180 coupled to the end of the tool driver 170 may receive and guide a surgical instrument 190 (e.g., end effector, camera, etc.). Furthermore, the robotic arm 160 may include a plurality of links that are actuated so as to position and orient the tool driver 170, which actuates the surgical instrument 190. The robotic surgical system may further include a control tower 152 (e.g., including a power supply, computing equipment, etc.) and/or other suitable equipment for supporting functionality of the robotic components.

In some variations, a user (such as a surgeon or other operator) may use a user console 100 to remotely manipulate the robotic arms 160 and/or surgical instruments (e.g., tele-operation). The user console 100 may be located in the same procedure room as the robotic system 150, as shown in FIG. 1A. In other embodiments, the user console 100 may be located in an adjacent or nearby room, or tele-operated from a remote location in a different building, city, or country. In one example, the user console 100 comprises a seat 110, foot-operated controls 120, one or more handheld user interface devices 122, and at least one user display 130 configured to display, for example, a view of the surgical site inside a patient. For example, as shown in the exemplary user console shown in FIG. 1A, a user located in the seat 110 and viewing the user display 130 may manipulate the foot-operated controls 120 and/or handheld user interface devices to remotely control the robotic arms 160 and/or surgical instruments.

In some variations, a user may operate the robotic surgical system 150 in an "over the bed" (OTB) mode, in which the user is at the patient's side and simultaneously manipulating a robotically-driven tool driver/end effector attached thereto (e.g., with a handheld user interface device 122 held in one hand) and a manual laparoscopic tool. For example, the user's left hand may be manipulating a handheld user interface device 122 to control a robotic surgical component, while the user's right hand may be manipulating a manual laparoscopic tool. Thus, in these variations, the user may perform both robotic-assisted MIS and manual laparoscopic techniques on a patient.

During an exemplary procedure or surgery, the patient is prepped and draped in a sterile fashion, and anesthesia is achieved. Initial access to the surgical site may be performed manually with the robotic system 150 in a stowed configuration or withdrawn configuration to facilitate access to the surgical site. Once access is completed, initial positioning and/or preparation of the robotic system may be performed. During the surgical procedure, a surgeon or other user in the user console 100 may utilize the foot-operated controls 120 and/or user interface devices 122 to manipulate various end effectors and/or imaging systems to perform the procedure. Manual assistance may also be provided at the procedure table by sterile-gowned personnel, who may perform tasks including but not limited to retracting organs, or performing manual repositioning or tool exchange involving one or more robotic arms 160. Non-sterile personnel may also be present to assist the surgeon at the user console 100. When the procedure or surgery is completed, the robotic system 150 and/or user console 100 may be configured or set in a state to facilitate one or more post-operative procedures, including but not limited to robotic system 150 cleaning and/or sterilization, and/or healthcare record entry or printout, whether electronic or hard copy, such as via the user console 100.

In FIG. 1A, the robotic arms 160 are shown with a table-mounted system, but in other embodiments, the robotic arms may be mounted in a cart, ceiling or sidewall, or other suitable support surface. The communication between the robotic system 150, the user console 100, and any other displays may be via wired and/or wireless connection(s). Any wired connections may be optionally built into the floor and/or walls or ceiling. The communication between the user console 100 and the robotic system 150 may be wired and/or wireless, and may be proprietary and/or performed using any of a variety of data communication protocols. In still other variations, the user console 100 does not include an integrated display 130, but may provide a video output that can be connected to output to one or more generic displays, including remote displays accessible via the internet or network. The video output or feed may also be encrypted to ensure privacy and all or portions of the video output may be saved to a server or electronic healthcare record system.

In other examples, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Virtual Reality System

Figure 2A:
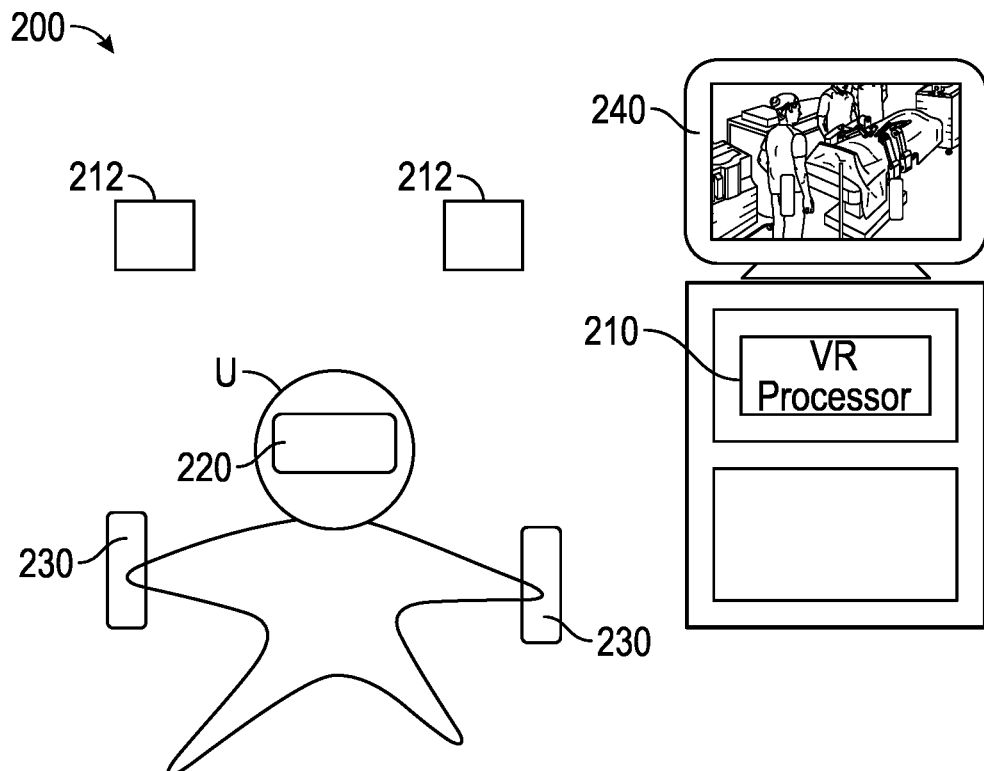
FIG. 2A is a schematic illustration of one variation of a virtual reality system.
Figure 2B:
FIG. 2B is a schematic illustration of an immersive display for displaying an immersive view of a virtual reality environment.

A virtual reality system for providing a virtual robotic surgical environment is described herein. As shown in FIG. 2A, a virtual reality system 200 may include a virtual reality processor 210 (e.g., a processor in a computer implementing instructions stored in memory) for generating a virtual robotic surgical environment, a head-mounted display 220 wearable by a user U, and one or more handheld controllers 230 manipulable by the user U for interacting with the virtual robotic surgical environment. As shown in FIG. 2B, the head-mounted display 220 may include an immersive display 222 for displaying the virtual robotic surgical environment to the user U (e.g., with a first-person perspective view of the virtual environment). The immersive display may, for example, be a stereoscopic display provided by eyepiece assemblies. In some variations, the virtual reality system 200 may additionally or alternatively include an external display 240 for displaying the virtual robotic surgical environment. The immersive display 222 and the external display 240, if both are present, may be synchronized to show the same or similar content.

As described in further detail herein, the virtual reality system (and variations thereof, as further described herein) may serve as a useful tool with respect to robotic surgery, in applications including but not limited to training, simulation, and/or collaboration among multiple persons. More specific examples of applications and uses of the virtual reality system are described herein.

Generally, the virtual reality processor is configured to generate a virtual robotic surgical environment within which a user may navigate around a virtual operating room and interact with virtual objects via the head-mounted display and/or handheld controllers. For example, a virtual robotic surgical system may be integrated into a virtual operating room, with one or more virtual robotic components having three-dimensional meshes and selected characteristics (e.g., dimensions and kinematic constraints of virtual robotic arms and/or virtual surgical tools, number and arrangement thereof, etc.). Other virtual objects, such as a virtual control towers or other virtual equipment representing equipment supporting the robotic surgical system, a virtual patient, a virtual table or other surface for the patient, virtual medical staff, a virtual user console, etc., may also be integrated into the virtual reality operating room.

In some variations, the head-mounted display 220 and/or the handheld controllers 230 may be modified versions of those included in any suitable virtual reality hardware system that is commercially available for applications including virtual and augmented reality environments (e.g., for gaming and/or military purposes) and are familiar to one of ordinary skill in the art. For example, the head-mounted display 220 and/or the handheld controllers 230 may be modified to enable interaction by a user with a virtual robotic surgical environment (e.g., a handheld controller 230 may be modified as described below to operate as a laparoscopic handheld controller). The handheld controller may include, for example, a carried device (e.g., wand, remote device, etc.) and/or a garment worn on the user's hand (e.g., gloves, rings, wristbands, etc.) and including sensors and/or configured to cooperate with external sensors to thereby provide tracking of the user's hand(s), individual finger(s), wrist(s), etc. Other suitable controllers may additionally or alternatively be used (e.g., sleeves configured to provide tracking of the user's arm(s)).

Generally, a user U may don the head-mounted display 220 and carry (or wear) at least one handheld controller 230 while he or she moves around a physical workspace, such as a training room. While wearing the head-mounted display 220, the user may view an immersive first-person perspective view of the virtual robotic surgical environment generated by the virtual reality processor 210 and displayed onto the immersive display 222. As shown in FIG. 2B, the view displayed onto the immersive display 222 may include one or more graphical representations 230' of the handheld controllers (e.g., virtual models of the handheld controllers, virtual models of human hands in place of handheld controllers or holding handheld controllers, etc.). A similar first-person perspective view may be displayed onto an external display 240 (e.g., for assistants, mentors, or other suitable persons to view). As the user moves and navigates within the workspace, the virtual reality processor 210 may change the view of the virtual robotic surgical environment displayed on the immersive display 222 based at least in part on the location and orientation of the head-mounted display (and hence the user's location and orientation), thereby allowing the user to feel as if he or she is exploring and moving within the virtual robotic surgical environment.

Additionally, the user may further interact with the virtual robotic surgical environment by moving and/or manipulating the handheld controllers 230. For example, the handheld controllers 230 may include one or more buttons, triggers, touch-sensitive features, scroll wheels, switches, and/or other suitable interactive features that the user may manipulate to interact with the virtual environment. As the user moves the handheld controllers 230, the virtual reality processor 210 may move the graphical representations 230' of the handheld controllers (or a cursor or other representative icon) within the virtual robotic surgical environment. Furthermore, engaging one or more interactive features of the handheld controllers 230 may enable the user to manipulate aspects of the virtual environment. For example, the user may move a handheld controller 230 until the graphical representation 230' of the handheld controller is in proximity to a virtual touchpoint (e.g., selectable location) on a virtual robotic arm in the environment, engage a trigger or other interactive feature on the handheld controller 230 to select the virtual touchpoint, then move the handheld controller 230 while engaging the trigger to drag or otherwise manipulate the virtual robotic arm via the virtual touchpoint. Other examples of user interactions with the virtual robotic surgical environment are described in further detail below.

In some variations, the virtual reality system may engage other senses of the user. For example, the virtual reality system may include one or more audio devices (e.g., headphones for the user, speakers, etc.) for relaying audio feedback to the user. As another example, the virtual reality system may provide tactile feedback, such as vibration, in one or more of the handheld controllers 230, the head-mounted display 220, or other haptic devices contacting the user (e.g., gloves, wristbands, etc.).

Virtual Reality Processor

Figure 3:
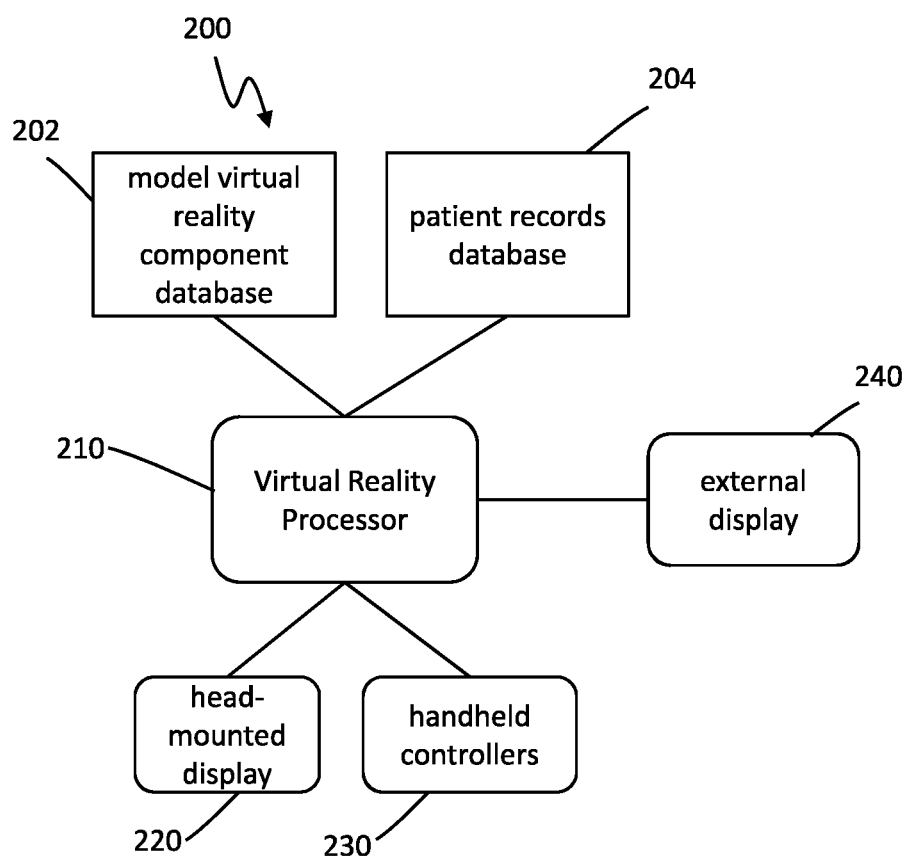
FIG. 3 is a schematic illustration of components of a virtual reality system.

The virtual reality processor 210 may be configured to generate a virtual robotic surgical environment within which a user may navigate around a virtual operating room and interact with virtual objects. A general schematic illustrating an exemplary interaction between the virtual reality processor and at least some components of the virtual reality system is shown in FIG. 3.

In some variations, the virtual reality processor 210 may be in communication with hardware components such as the head-mounted display 220, and/or handheld controllers 230.

For example, the virtual reality processor 210 may receive input from sensors in the head-mounted display 220 to determine location and orientation of the user within the physical workspace, which may be used to generate a suitable, corresponding first-person perspective view of the virtual environment to display in the head-mounted display 220 to the user. As another example, the virtual reality control 210 may receive input from sensors in the handheld controllers 230 to determine location and orientation of the handheld controllers 230, which may be used to generate suitable graphical representations of the handheld controllers 230 to display in the head-mounted display 220 to the user, as well as translate user input (for interacting with the virtual environment) into corresponding modifications of the virtual robotic surgical environment. The virtual reality processor 210 may be coupled to an external display 240 (e.g., a monitor screen) that is visible to the user in a non-immersive manner and/or to other persons such as assistants or mentors who may wish to view the user's interactions with the virtual environment.

In some variations, the virtual reality processor 210 (or multiple processor machines) may be configured to execute one or more software applications for generating the virtual robotic surgical environment. For example, as shown in FIG. 4, the virtual reality processor 210 may utilize at least two software applications, including a virtual operating environment application 410 and a kinematics application 420. The virtual operating environment application and the kinematics application may communicate via a client-server model. For example, the virtual operating environment application may operate as a client, while the kinematics application may operate as a server. The virtual operation environment application 410 and the kinematics application 420 may be executed on the same processing machine, or on separate processing machines coupled via a computer network (e.g., the client or the server may be a remote device, or the machines may be on a local computer network). Additionally, it should be understood that in other variations, the virtual operating environment application 410 and/or the kinematics application 420 may interface with other software components. In some variations, the virtual operating environment application 410 and the kinematics application 520 may invoke one or more application program interfaces (APIs), which define the manner in which the applications communicate with one another.

The virtual operating environment 410 may allow for a description or definition of the virtual operating room environment (e.g., the operating room, operating table, control tower or other components, user console, robotic arms, table adapter links coupling robotic arms to the operating table, etc.). At least some descriptions of the virtual operating room environment may be saved (e.g., in a model virtual reality component database 202) and provided to the processor as configuration files. For example, in some variations, as shown in FIG. 3, the virtual reality processor (such as through the virtual operating environment application 410 described above) may be in communication with a model virtual reality component database 202 (e.g., stored on a server, local or remote hard drive, or other suitable memory). The model virtual reality component database 202 may store one or more configuration files describing virtual components of the virtual robotic surgical environment. For example, the database 202 may store files describing different kinds of operating rooms (e.g., varying in room shape or room dimensions), operating tables or other surfaces on which a patient lies (e.g., varying in size, height, surfaces, material construction, etc.), control towers (e.g., varying in size and shape), user console (e.g., varying in user seat design), robotic arms (e.g., design of arm links and joints, number and arrangement thereof, number and location of virtual touchpoints on the arm, etc.), table adapter links coupling robotic arms to an operating table (e.g., design of table adapter links and joints, number and arrangement thereof, etc.), patient types (e.g., varying in sex, age, weight, height, girth, etc.) and/or medical personnel (e.g., generic graphical representations of people, graphical representations of actual medical staff, etc.). As one specific example, a configuration file in Unified Robot Description Format (URDF) may store a configuration of a particular robotic arm, including definitions or values for fields such as number of arm links, number of arm joints connecting the arm links, length of each arm link, diameter or girth of each arm link, mass of each arm link, type of arm joint (e.g., roll, pitch, yaw etc.), etc. Additionally, kinematic constraints may be loaded as a "wrapper" over a virtual robotic component (e.g., arm) to further define the kinematic behavior of the virtual robotic component. In other variations, the virtual reality processor 210 may receive any suitable descriptions of virtual components to load and generate in the virtual robotic surgical environment. Accordingly, the virtual reality processor 210 may receive and utilize different combinations of configuration files and/or other descriptions of virtual components to generate particular virtual robotic surgical environments.

In some variations, as shown in FIG. 3, the virtual reality processor 210 may additionally or alternatively be in communication with a patient records database 204, which may store patient-specific information. Such patient-specific information may include, for example, patient imaging data (e.g., X-ray, MRI, CT, ultrasound, etc.), medical histories, and/or patient metrics (e.g., age, weight, height, etc.), though other suitable patient-specific information may additionally or alternatively be stored in the patient records database 204. When generating the virtual robotic surgical environment, the virtual reality processor 210 may receive patient-specific information from the patient records database 204 and integrate at least some of the received information into the virtual reality environment. For example, a realistic representation of the patient's body or other tissue may be generated and incorporated into the virtual reality environment (e.g., a 3D model generated from a combined stack of 2D images, such as MRI images), which may be useful, for example, for determining desirable arrangement of robotic arms around the patient, optimal port placement, etc. specific to a particular patient, as further described herein. As another example, patient imaging data may be overlaid over a portion of the user's field of view of the virtual environment (e.g., overlaying an ultrasound image of a patient's tissue over the virtual patient's tissue).

In some variations, the virtual reality processor 210 may embed one or more kinematics algorithms via the kinematics application 420 to at least partially describe behavior of one or more components of the virtual robotic system in the virtual robotic surgical environment. For example, one or more algorithms may define how a virtual robotic arm responds to user interactions (e.g., moving the virtual robotic arm by selection and manipulation of a touchpoint on the virtual robotic arm), or how a virtual robotic arm operates in a selected control mode. Other kinematics algorithms, such as those defining operation of a virtual tool driver, a virtual patient table, or other virtual components, may additionally or alternatively be embedded in the virtual environment. By embedding in the virtual environment one or more kinematics algorithms that accurately describe behavior of an actual (real) robotic surgical system, the virtual reality processor 210 may permit the virtual robotic surgical system to function accurately or realistically compared to a physical implementation of a corresponding real robotic surgical system. For example, the virtual reality processor 210 may embed at least one control algorithm that represents or corresponds to one or more control modes defining movement of a robotic component (e.g., arm) in an actual robotic surgical system.

For example, the kinematics application 420 may allow for a description or definition of one or more virtual control modes, such as for the virtual robotic arms or other suitable virtual components in the virtual environment. Generally, for example, a control mode for a virtual robotic arm may correspond to a function block that enables the virtual robotic arm to perform or carry out a particular task. For example, as shown in FIG. 4, a control system 430 may include multiple virtual control modes 432, 434, 436, etc. governing actuation of at least one joint in the virtual robotic arm. The virtual control modes 432, 434, 436, etc. may include at least one primitive mode (which governs the underlying behavior for actuation of at least one joint) and/or at least one user mode (which governs higher level, task-specific behavior and may utilize one or more primitive modes). In some variations, a user may activate a virtual touchpoint surface of a virtual robotic arm or other virtual object, thereby triggering a particular control mode (e.g., via a state machine or other controller). In some variations, a user may directly select a particular control mode through, for example, a menu displayed in the first-person perspective view of the virtual environment.

Examples of primitive virtual control modes include, but are not limited to, a joint command mode (which allows a user to directly actuate a single virtual joint individually, and/or multiple virtual joints collectively), a gravity compensation mode (in which the virtual robotic arm holds itself in a particular pose, with particular position and orientation of the links and joints, without drifting downward due to simulated gravity), and trajectory following mode (in which the virtual robotic arm may move to follow a sequence of one or more Cartesian or other trajectory commands). Examples of user modes that incorporate one or more primitive control modes include, but are not limited to, an idling mode (in which the virtual robotic arm may rest in a current or default pose awaiting further commands), a setup mode (in which the virtual robotic arm may transition to a default setup pose or a predetermined template pose for a particular type of surgical procedure), and a docking mode (in which the robotic arm facilitates the process in which the user attaches the robotic arm to a part, such as with gravity compensation, etc.).

Generally, the virtual operating environment application 410 and the kinematics application 420 may communicate with each other via a predefined communication protocol, such as an application program interface (APIs) that organizes information (e.g., status or other characteristics) of virtual objects and other aspects of the virtual environment. For example, the API may include data structures that specify how to communicate information about virtual objects such as a virtual robotic arm (in whole and/or on a segment-by-segment basis) a virtual table, a virtual table adapter connecting a virtual arm to the virtual table, a virtual cannula, a virtual tool, a virtual touchpoint for facilitating user interaction with the virtual environment, user input system, handheld controller devices, etc. Furthermore, the API may include one or more data structures that specify how to communicate information about events in the virtual environment (e.g., a collision event between two virtual entities) or other aspects relating to the virtual environment (e.g., reference frame for displaying the virtual environment, control system framework, etc.). Exemplary data structures and exemplary fields for containing their information are listed and described in FIGS. 4B and 4C, though it should be understood that other variations of the API may include any suitable types, names, and numbers of data structures and exemplary field structures.

Figure 4A:
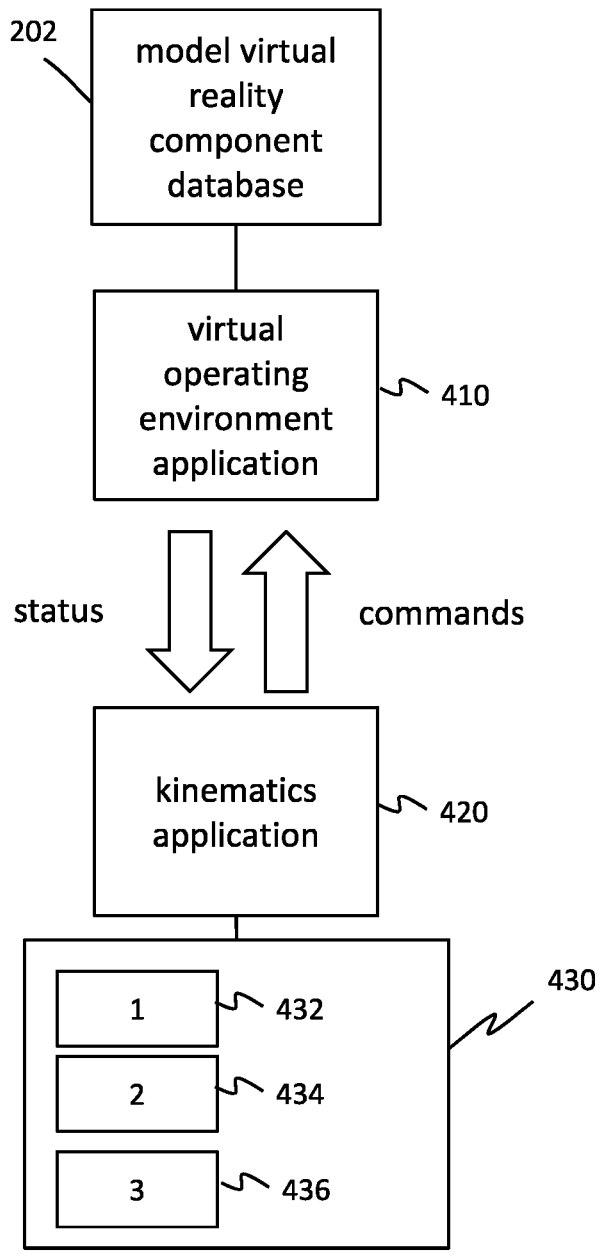
FIG. 4A is an exemplary structure for a communication between a virtual reality environment application and a kinematics application for use in a virtual reality system.

In some variations, as generally illustrated schematically in FIG. 4A, the virtual operating environment application 410 passes status information to the kinematics application 420, and the kinematics application 420 passes commands to the virtual operating environment application 410 via the API, where the commands are generated based on the status information and subsequently used by the virtual reality processor 210 to generate changes in the virtual robotic surgical environment. For example, a method for embedding one or more kinematics algorithms in a virtual robotic surgical environment for control of a virtual robotic arm may include passing status information regarding at least a portion of the virtual robotic arm from the virtual operating environment application 410 to the kinematics application 420, algorithmically determining an actuation command to actuate at least one virtual joint of the virtual robotic arm, and passing the actuation command from the kinematics application 420 to virtual operating environment application 410. The virtual reality processor 210 may subsequently move the virtual robotic arm in accordance with the actuation command.

As an illustrative example for controlling a virtual robotic arm, a gravity compensation control mode for a virtual robotic arm may be invoked, thereby requiring one or more virtual joint actuation commands in order to counteract simulated gravity forces on the virtual joints in the virtual robotic arm. The virtual operating environment application 410 may pass to the kinematics application 420 relevant status information regarding the virtual robotic arm (e.g., position of at least a portion of the virtual robotic arm, position of the virtual patient table to which the virtual robotic arm is mounted, position of a virtual touchpoint that the user may have manipulated to move the virtual robotic arm, joint angles between adjacent virtual arm links) and status information (e.g., direction of simulated gravitational force on the virtual robotic arm). Based on the received status information from the virtual operating environment application 410 and known kinematic and/or dynamic properties of the virtual robotic arm and/or virtual tool drive attached to the virtual robotic arm (e.g., known from a configuration file, etc.), the control system 430 may algorithmically determine what actuated force at each virtual joint is required to compensate for the simulated gravitational force acting on that virtual joint. For example, the control system 430 may utilize a forward kinematic algorithm, an inverse algorithm, or any suitable algorithm. Once the actuated force command for each relevant virtual joint of the virtual robotic arm is determined, the kinematics application 420 may send the force commands to the virtual operating environment application 410. The virtual reality processor subsequently may actuate the virtual joints of the virtual robotic arm in accordance with the force commands, thereby causing the virtual robotic arm to be visualized as maintaining its current pose despite the simulated gravitational force in the virtual environment (e.g., instead of falling down or collapsing under simulated gravitational force).

Another example for controlling a virtual robotic arm is trajectory following for a robotic arm. In trajectory following, movement of the robotic arm may be programmed then emulated using the virtual reality system. Accordingly, when the system is used to emulate a trajectory planning control mode, the actuation command generated by a kinematics application may include generating an actuated command for each of a plurality of virtual joints in the virtual robotic arm. This set of actuated commands may be implemented by a virtual operating environment application to move the virtual robotic arm in the virtual environment, thereby allowing testing for collision, volume or workspace of movement, etc.

Other virtual control algorithms for the virtual robotic arm and/or other virtual components (e.g., virtual table adapter links coupling the virtual robotic arm to a virtual operating table) may be implemented via similar communication between the virtual operating environment application 410 and the kinematics application 420.

Although the virtual reality processor 210 is generally referred to herein as a single processor, it should be understood that in some variations, multiple processors may be used to perform the processors described herein. The one or more processors may include, for example, a processor of a general purpose computer, a special purpose computer or controller, or other programmable data processing apparatus or component, etc. Generally, the one or more processors may be configured to execute instructions stored on any suitable computer readable media. The computer readable media may include, for example, magnetic media, optical media, magneto-optical media and hardware devices that are specially configured to store and execute program code, such as application-specific integrated circuits (ASICs), programmable logic devices (PLDs), ROM and RAM devices, flash memory, EEPROMs, optical devices (e.g., CD or DVD), hard drives, floppy drives, or any suitable device. Examples of computer program code include machine code, such as produced by a compiler, and files containing higher-level code that are executed by a computer using an interpreter. For example, one variation may be implemented using C++, JAVA, or other suitable object-oriented programming language and development tools. As another example, another variation may be implemented in hardwired circuitry in place of, or in combination with, machine-executable software instructions.

Head-Mounted Display and Handheld Controllers

As shown in FIG. 2A, a user U may wear a head-mounted display 220 and/or hold one or more handheld controllers 230. The head-mounted display 220 and handheld controllers 230 may generally enable a user to navigate and/or interact with the virtual robotic surgical environment generated by the virtual reality processor 210. The head-mounted display 220 and/or handheld controllers 230 may communicate signals to the virtual reality processor 210 via a wired or wireless connection.

In some variations, the head-mounted display 220 and/or the handheld controllers 230 may be modified versions of those included in any suitable virtual reality hardware system that is commercially available for applications including virtual and augmented reality environments. For example, the head-mounted display 220 and/or the handheld controllers 230 may be modified to enable interaction by a user with a virtual robotic surgical environment (e.g., a handheld controller 230 may be modified as described below to operate as a laparoscopic handheld controller). In some variations, the virtual reality system may further include one or more tracking emitters 212 that emit infrared light into a workspace for the user U. The tracking emitters 212 may, for example, be mounted on a wall, ceiling, fixture, or other suitable mounting surface. Sensors may be coupled to outward-facing surfaces of the head-mounted display 220 and/or handheld controllers 230 for detecting the emitted infrared light. Based on the location of any sensors that detect the emitted light and when such sensors detect the emitted light after the light is emitted, the virtual reality processor 220 may be configured to determine (e.g., through triangulation) the location and orientation of the head-mounted display 220 and/or handheld controllers 230 within the workspace. In other variations, other suitable means (e.g., other sensor technologies such as accelerometers or gyroscopes, other sensor arrangements, etc.) may be used to determine location and orientation of the head-mounted display 220 and handheld controllers 230.

In some variations, the head-mounted display 220 may include straps (e.g., with buckles, elastic, snaps, etc.) that facilitate mounting of the display 220 to the user's head. For example, the head-mounted display 220 may be structured similar to goggles, a headband or headset, a cap, etc. The head-mounted display 220 may include two eyepiece assemblies providing a stereoscopic immersive display, though alternatively may include any suitable display.

The handheld controllers 230 may include interactive features that the user may manipulate to interact with the virtual robotic surgical environment. For example, the handheld controllers 230 may include one or more buttons, triggers, touch-sensitive features, scroll wheels, switches, and/or other suitable interactive features. Additionally, the handheld controllers 230 may have any of various form factors, such as a wand, pinchers, generally round shapes (e.g., ball or egg-shaped), etc. In some variations, the graphical representations 230' displayed on the head-mounted display 220 and/or external display 240 may generally mimic the form factor of the actual, real handheld controllers 230. In some variations, the handheld controller may include a carried device (e.g., wand, remote device, etc.) and/or a garment worn on the user's hand (e.g., gloves, rings, wristbands, etc.) and including sensors and/or configured to cooperate with external sensors to thereby provide tracking of the user's hand(s), individual finger(s), wrist(s), etc. Other suitable controllers may additionally or alternatively be used (e.g., sleeves configured to provide tracking of the user's arm(s)).

Laparoscopic Handheld Controller

Figure 5A:
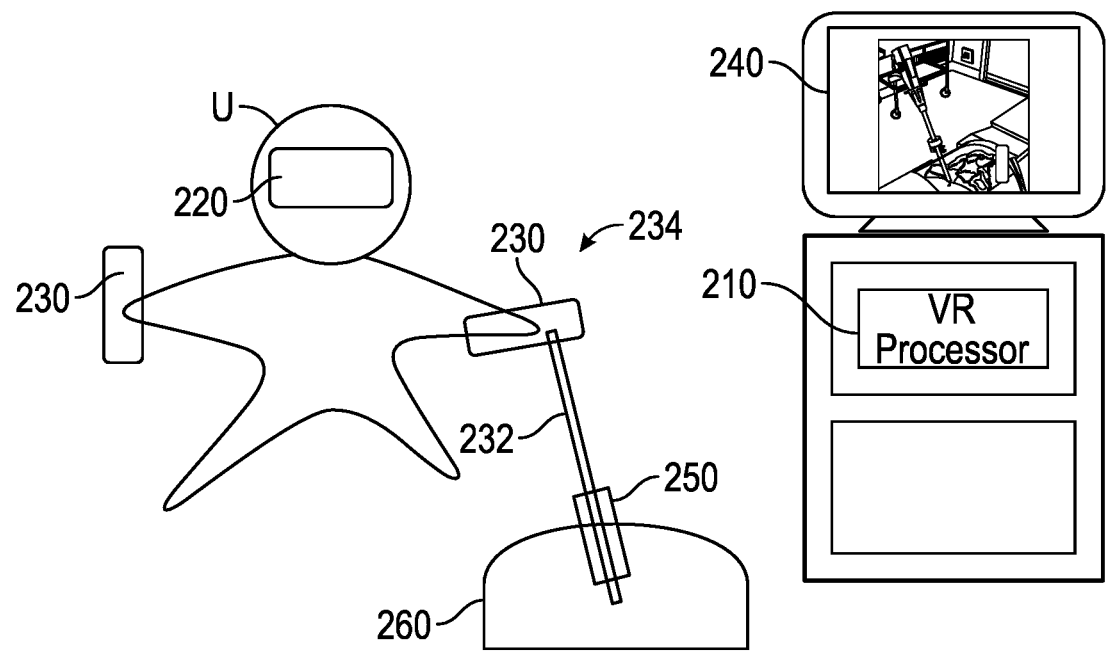
FIG. 5A is a schematic illustration of another variation of a virtual reality system including an exemplary variation of a laparoscopic handheld controller.

In some variations, as shown in the schematic of FIG. 5A, the handheld controller 230 may further include at least one tool feature 232 that is representative of at least a portion of a manual laparoscopic tool, thereby forming a laparoscopic handheld controller 234 that may be used to control a virtual manual laparoscopic tool. Generally, for example, the tool feature 232 may function to adapt the handheld controller 230 into a controller substantially similar in form (e.g., user feel and touch) to a manual laparoscopic tool. The laparoscopic handheld controller 234 may be communicatively coupled to the virtual reality processor 210 for manipulating a virtual manual laparoscopic tool in the virtual robotic surgical environment, and may help enable the user to feel as if he or she is using an actual manual laparoscopic tool while interacting with the virtual robotic surgical environment. In some variations the laparoscopic handheld device may be a mock-up (e.g., facsimile or genericized version) of a manual laparoscopic tool, while in other variations the laparoscopic handheld device may be a functioning manual laparoscopic tool. Movements of at least a portion of the laparoscopic handheld controller may be mapped by the virtual reality controller to correspond to movements of the virtual manual laparoscopic tool. Thus, in some variations, the virtual reality system may simulate use of a manual laparoscopic tool for manual MIS.

As shown in FIG. 5A, the laparoscopic handheld controller 234 may be used with a mock patient setup to further simulate the feel of a virtual manual laparoscopic tool. For example, the laparoscopic handheld controller 234 may be inserted into a cannula 250 (e.g., an actual cannula used in MIS procedures to provide realistic feel of a manual tool within a cannula, or a suitable representation thereof, such as a tube with a lumen for receiving a tool shaft portion of the laparoscopic handheld controller 234). The cannula 250 may be placed in a mock patient abdomen 260, such as a foam body with one or more insertion sites or ports for receiving the cannula 250. Alternatively, other suitable mock patient setups may be used, such as a cavity providing resistance (e.g., with fluid, etc.) with similar feel as an actual patient abdomen.

Figure 5B:
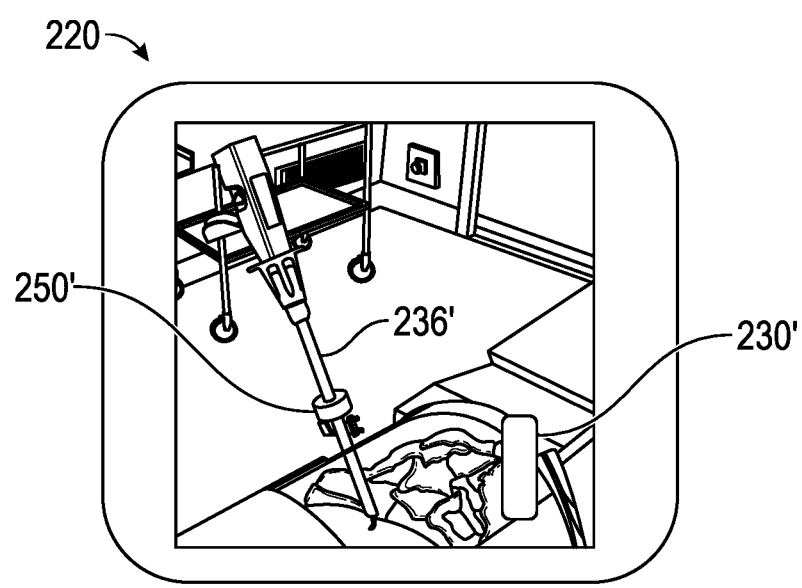
FIG. 5B is a schematic illustration of an immersive display for displaying an immersive view of a virtual reality environment including a virtual manual laparoscopic tool controlled by the laparoscopic handheld controller.

Additionally, as shown in FIG. 5B, the virtual reality processor may generate a virtual robotic surgical environment including a virtual manual laparoscopic tool 236' and/or a virtual cannula 250' relative to a virtual patient (e.g., the graphical representation 250' of the cannula depicted as inserted in the virtual patient). As such, the virtual environment with the virtual manual laparoscopic tool 236' and virtual cannula 250' may be displayed on the immersive display provided by the head-mounted display 220, and/or the external display 240. A calibration procedure may be performed to map the laparoscopic handheld controller 234 to the virtual manual laparoscopic tool 236' within the virtual environment. Accordingly, as the user moves and manipulates the laparoscopic handheld controller 234, the combination of the at least one tool feature 234 and the mock patient setup may allow the user to tactilely feel as if he or she is using a manual laparoscopic tool in the virtual robotic surgical environment. Likewise, as the user moves and manipulates the laparoscopic handheld controller 234, the corresponding movements of the virtual manual laparoscopic tool 236' may allow the user to visualize the simulation that he or she is using a manual laparoscopic tool in the virtual robotic surgical environment.

In some variations, the calibration procedure for the laparoscopic handheld controller generally maps the laparoscopic handheld controller 234 to the virtual manual laparoscopic tool 236'. For example, generally, the calibration procedure may "zero" its position relative to a reference point within the virtual environment. In an exemplary calibration procedure, the user may insert the laparoscopic handheld controller through a cannula 250 into a mock patient abdomen 260, which may be placed on a table in front of the user (e.g., at a height that is representative of the height of a real operating patient table). The user may continue inserting the laparoscopic handheld controller into the mock patient abdomen 260 into a suitable depth representative of depth achieved during a real laparoscopic procedure. Once the laparoscopic handheld controller is suitably placed in the mock patient abdomen 260, the user may provide an input (e.g., squeeze a trigger or push a button on the laparoscopic handheld controller, by voice command, etc.) to confirm and orient the virtual patient to the location and height of the mock patient abdomen 260. Additionally, other aspects of the virtual environment may be calibrated to align with the real, tangible aspects of the system, such as by depicting virtual components adjustably movable to target locations and allowing user input to confirm new alignment of the virtual component with target locations (e.g., by squeezing a trigger or pushing a button on the laparoscopic handheld controller, voice command, etc.). Orientation of virtual components (e.g., rotational orientation of a shaft) may be adjusted with a touchpad, trackball, or other suitable input on the laparoscopic handheld controller or other device. For example, the virtual operating room may be aligned with the real room in which the user is standing, a distal end of the virtual cannula or trocar may be aligned with the real entry location in the mock patient abdomen, etc. Furthermore, in some variations, a virtual end effector (e.g., endocutter, clipper) may be located and oriented via the laparoscopic handheld controller to a new target location and orientation in similar manners.

In some variations, as shown in FIG. 5B, the system may include both a handheld controller 230 and a laparoscopic handheld controller 234. Accordingly, the virtual reality processor may generate a virtual environment including both a graphical representation 230' of a handheld controller 230 (with no laparoscopic attachment) and a virtual manual laparoscopic tool 236' as described above. The handheld controller 230 may be communicatively coupled to the virtual reality processor 210 for manipulating at least one virtual robotic arm, and the laparoscopic handheld controller 234 may be communicatively coupled to the virtual reality processor 210 for manipulating a virtual manual laparoscopic tool 236'. Thus, in some variations, the virtual reality system may simulate an "over the bed" mode of using a robotic surgical system, in which an operator is at the patient's side and manipulating both a robotic arm (e.g., with one hand) providing robotic-assisted MIS, and a manual laparoscopic tool providing manual MIS.

The tool feature 232 may include any suitable feature generally approximating or representing a portion of a manual laparoscopic tool. For example, the tool feature 232 may generally approximate a laparoscopic tool shaft (e.g., include an elongated member extending from a handheld portion of the controller). As another example, the tool feature 232 may include a trigger, button, or other laparoscopic interactive feature similar to that present on a manual laparoscopic tool that engages an interactive feature on the handheld controller 230 but provides a realistic form factor mimicking the feel of a manual laparoscopic tool (e.g., the tool feature 232 may include a larger trigger having a realistic form factor that is overlaid with and engages a generic interactive feature on the handheld controller 230). As yet another example, the tool feature 232 may include selected materials and/or masses to create a laparoscopic handheld controller 234 having a weight distribution that is similar to a particular kind of manual laparoscopic tool. In some variations, the tool feature 232 may include plastic (e.g., polycarbonate, acrylonitrile butadiene styrene (ABS), nylon, etc.) that is injection molded, machined, 3D-printed, or other suitable material shaped in any suitable fashion. In other variations, the tool feature 232 may include metal or other suitable material that is machined, casted, etc.

In some variations, the tool feature 236 may be an adapter or other attachment that is formed separately from the handheld controller 230 and coupled to the handheld controller 230 via fasteners (e.g., screws, magnets, etc.), interlocking features (e.g., threads or snap fit features such as tabs and slots, etc.), epoxy, welding (e.g., ultrasonic welding), etc. The tool feature 236 may be reversibly coupled to the handheld controller 230. For example, the tool feature 236 may be selectively attached to the handheld controller 230 in order to adapt a handheld controller 230 when a laparoscopic-style handheld controller 230 is desired, while the tool feature 236 may be selectively detached from the handheld controller 230 when a laparoscopic-style handheld controller 230 is not desired. Alternatively, the tool feature 236 may be permanently coupled to the handheld portion 234, such as during manufacturing. Furthermore, in some variations, the handheld portion 234 and the tool feature 236 may be integrally formed (e.g., injection molded together as a single piece).

Figure 6A:
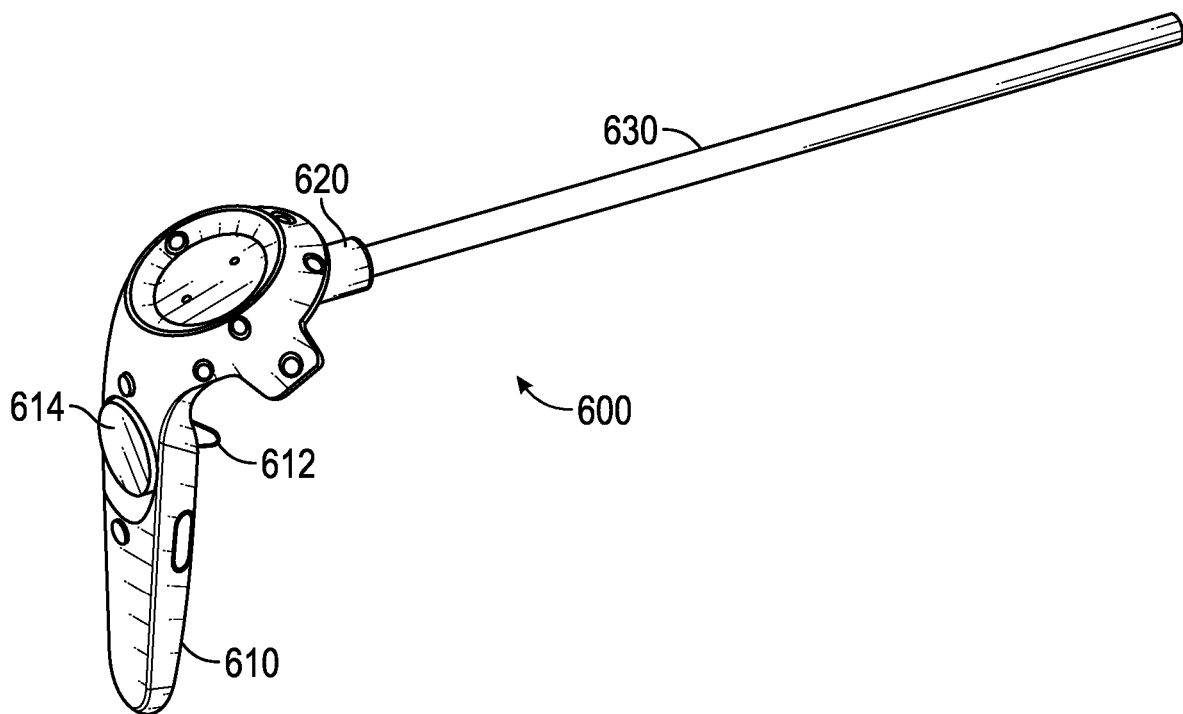
FIG. 6A is a perspective view of an exemplary variation of a laparoscopic handheld controller.
Figure 6B:
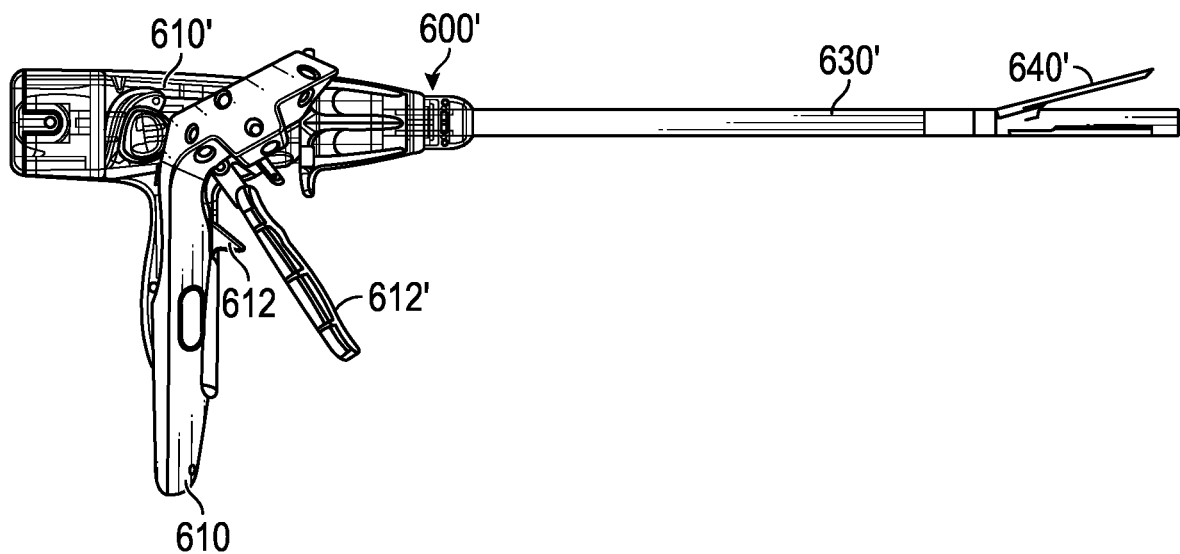
FIG. 6B is a schematic illustration of a virtual manual laparoscopic tool overlaid on part of the laparoscopic handheld controller shown in FIG. 6A.

One exemplary variation of a laparoscopic handheld controller is shown in FIG. 6A. The laparoscopic handheld controller 600 may include a handheld portion 610 (e.g., similar to handheld controller 230 described above), a tool shaft 630, and a shaft adapter 620 for coupling the tool shaft 630 to the handheld portion 610. As shown in FIG. 6B, the laparoscopic handheld controller 600 may generally be used to control a virtual manual laparoscopic stapler tool 600', though the laparoscopic handheld controller 600 may be used to control other kinds of virtual manual laparoscopic tools (e.g., scissors, dissectors, graspers, needleholders, probes, forceps, biopsy tools, etc. For example, the handheld portion 610 may be associated with a virtual handle 610' of the virtual manual laparoscopic stapler tool 600' having a stapler end effector 640', such that the user's manipulation of the handheld portion 610 is mapped to manipulation of the virtual handle 610'. Similarly, the tool shaft 630 may correspond to a virtual tool shaft 630' of the virtual manual laparoscopic stapler tool 600'. The tool shaft 630 and the virtual tool shaft 630' may be inserted into a cannula and a virtual cannula, respectively, such that movement of the tool shaft 630 relative to the cannula is mapped to movement of the virtual tool shaft 630' within the virtual cannula in the virtual robotic surgical environment.

The handheld portion 610 may include one or more interactive features, such as finger trigger 612 and/or button 614, which may receive user input from the user's fingers, palms, etc. and be communicatively coupled to a virtual reality processor. In this exemplary embodiment, the finger trigger 612 may be mapped to a virtual trigger 612' on the virtual manual laparoscopic stapler tool 600'. The virtual trigger 612' may be visualized as actuating the virtual end effector 640' (e.g., causing the virtual members of the virtual end effector 640' to close and fire staplers) for stapling virtual tissue in the virtual environment. Accordingly, when the user actuates the finger trigger 612 on the laparoscopic handheld controller, the signal from finger trigger 612 may be communicated to the virtual reality processor, which modifies the virtual manual laparoscopic stapler tool 600' to interact within the virtual environment in simulation of an actual manual laparoscopic stapler tool. In another variation, a trigger attachment may physically resemble (e.g., in shape and form) the virtual trigger 612' on the virtual manual laparoscopic stapler tool 600' and may be coupled to the finger trigger 612, which may enable the laparoscopic handheld controller 600 to even more closely mimic the user feel of the virtual manual laparoscopic stapler tool 600'.

Figure 6C:
FIGS. 6C-6E are a side view, a detailed partial perspective view, and a partial cross-sectional view, respectively, of the laparoscopic handheld controller shown in FIG. 6A.
Figure 6D:
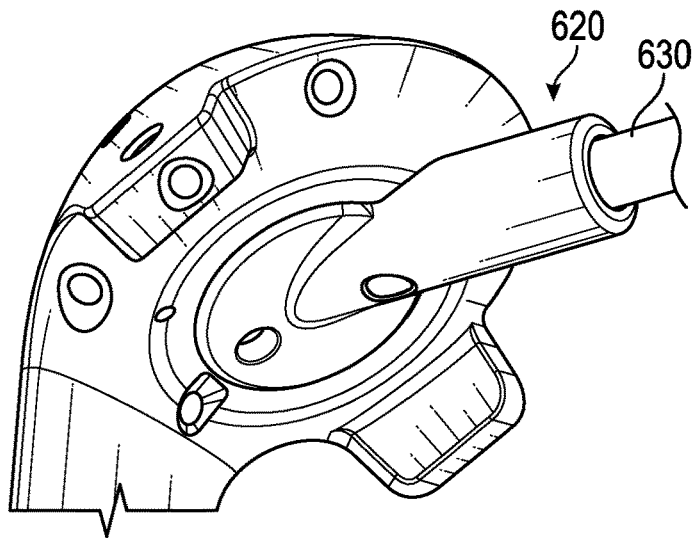
Figure 6E:
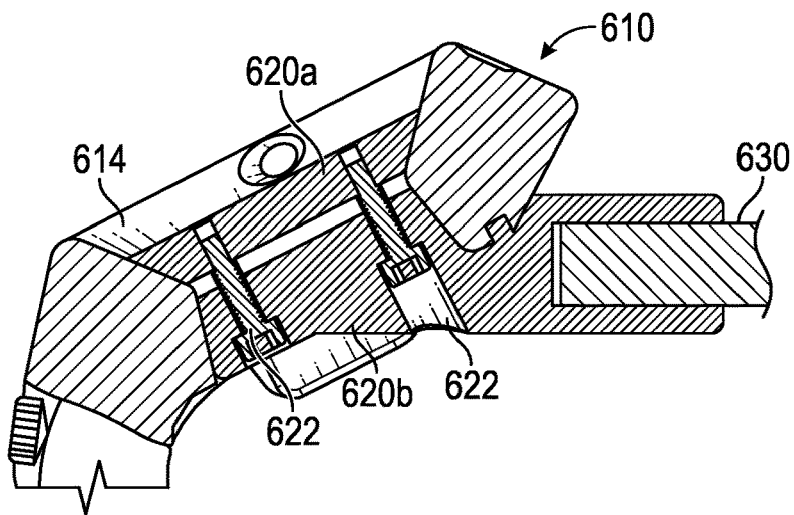
Figure 7:
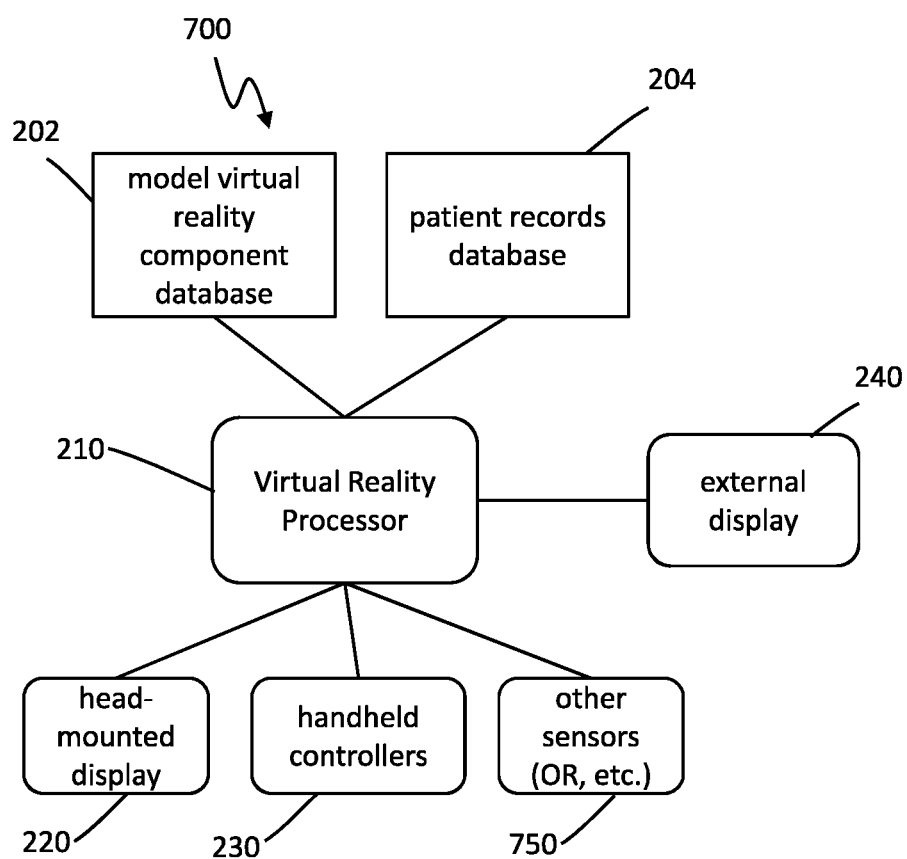
FIG. 7 is a schematic illustration of another variation of a virtual reality system interfacing with a robotic surgical environment.

As shown in FIGS. 6C-6E, the shaft adapter 620 may generally function to couple the tool shaft 630 to the handheld portion 610, which may, for example, adapt a handheld controller (similar to handheld controller 210 described above) into a laparoscopic handheld controller. The shaft adapter 620 may generally include a first end for coupling to the handheld portion 610 and a second end for coupling to the tool shaft 630. As shown best in FIG. 6E, the first end of the shaft adapter 620 may include a proximal portion 620a and distal portion 620b configured to clamp on a feature of the handheld portion 610. For example, the handheld portion 610 may include generally ring-like portion defining a central space 614 which receives the proximal portion 620a and the distal portion 620b. The proximal portion 620a and the distal portion 620b may clamp on either side of the ring-like portion at its inner diameter, and be fixed to the ring-like portion via fasteners (not shown) passing through fastener holes 622, thereby securing the shaft adapter 620 to the handheld portion 610. Additionally or alternatively, the shaft adapter 620 may couple to the handheld portion 610 in any suitable fashion, such as an interference fit, epoxy, interlocking features (e.g., between the proximal portion 620a and the distal portion 620b), etc. As also shown in FIG. 6E, the second end of the shaft adapter 620 may include a recess for receiving the tool shaft 620. For example, the recess may be generally cylindrical for receiving a generally cylindrical end of a tool shaft portion 630, such as through a press fit, friction fit, or other interference fit. Additionally or alternatively, the tool shaft 620 may be coupled to the shaft adapter 620 with fasteners (e.g., screws, bolts, epoxy, ultrasonic welding, etc.). The tool shaft 630 may be any suitable size (e.g., length, diameter) for mimicking or representing a manual laparoscopic tool.

In some variations, the shaft adapter 620 may be selectively removable from the handheld portion 610 for permitting selective use of the handheld portion 610 both as a standalone handheld controller (e.g., handheld controller 210) and as a laparoscopic handheld controller 600. Additionally or alternatively, the tool shaft 630 may be selectively removable from the shaft adapter 620 (e.g., although the shaft adapter 620 may be intentionally fixed to the handheld portion 610, the tool shaft 620 may be selectively removable from the shaft adapter 620 to convert the laparoscopic handheld control 600 to a standalone handheld controller 210).

Generally, the tool feature of the laparoscopic handheld controller 600, such as the shaft adapter 620 and the tool shaft 630, may be made of a rigid or semi-rigid plastic or metal, and may be formed through any suitable manufacturing process, such as 3D printing, injection molding, milling, turning, etc. The tool feature may include multiple kinds of materials, and/or weights or other masses to further simulate the user feel of a particular manual laparoscopic tool.

System Variations

One or more aspects of the virtual reality system described above may be incorporated into other variations of systems. For example, in some variations, a virtual reality system for providing a virtual robotic surgical environment may interface with one or more features of a real robotic surgical environment. For example, as shown in FIG. 3, a system 700 may include one or more processors (e.g., a virtual reality processor 210) configured to generate a virtual robotic surgical environment, and one or more sensors 750 in a robotic surgical environment, where the one or more sensors 750 is in communication with the one or more processors. Sensor information from the robotic surgical environment may be configured to detect status of an aspect of the robotic surgical environment, such for mimicking or replicating features of the robotic surgical environment in the virtual robotic surgical environment. For example, a user may monitor an actual robotic surgical procedure in a real operating room via a virtual reality system that interfaces with the real operating room (e.g., the user may interact with a virtual reality environment that is reflective of the conditions in the real operating room).

In some variations, one or more sensors 750 may be configured to detect status of at least one robotic component (e.g., a component of a robotic surgical system, such as a robotic arm, a tool driver coupled to a robotic arm, a patient operating table to which a robotic arm is attached, a control tower, etc.) or other component of a robotic surgical operating room. Such status may indicate, for example, position, orientation, speed, velocity, operative state (e.g., on or off, power level, mode), or any other suitable status of the component.

For example, one or more accelerometers may be coupled to a robotic arm link and be configured to provide information about the robotic arm link's position, orientation, and/or velocity of movement, etc. Multiple accelerometers on multiple robotic arms may be configured to provide information regarding impending and/or present collisions between robotic arms, between different links of a robotic arm, or between a robotic arm and a nearby obstacle having a known position.

As another example, one or more proximity sensors (e.g., infrared sensor, capacitive sensor) may be coupled to a portion of a robotic arm or other components of the robotic surgical system or surgical environment. Such proximity sensors may, for example, be configured to provide information regarding impending collisions between objects. Additionally or alternatively, contact or touch sensors may be coupled to a portion of a robotic arm or other components of the robotic surgical environment, and may be configured to provide information regarding a present collision between objects.

In another example, one or more components of the robotic surgical system or surgical environment may include markers (e.g., infrared markers) to facilitate optical tracking of the position, orientation, and/or velocity of various components, such as with overhead sensors monitoring the markers in the surgical environment. Similarly, the surgical environment may additionally or alternatively include cameras for scanning and/or modeling the surgical environment and its contents. Such optical tracking sensors and/or cameras may be configured to provide information regarding impending and/or present collisions between objects.

As another example, one or more sensors 750 may be configured to detect a status of a patient, a surgeon, or other surgical staff. Such status may indicate, for example, position, orientation, speed, velocity, and/or biological metrics such as heart rate, blood pressure, temperature, etc. For example, a heart rate monitor, a blood pressure monitor, thermometer, and/or oxygenation sensor, etc. may be coupled to the patient and enable a user to keep track of the patient's condition.

Generally, in these variations, a virtual reality processor 210 may generate a virtual robotic surgical environment similar to that described elsewhere herein. Additionally, upon receiving status information from the one or more sensors 750, the virtual reality processor 210 or other processor in the system may incorporate the detected status in any one or more suitable ways. For example, in one variation, the virtual reality processor 210 may be configured to generate a virtual reality replica or near-replica of a robotic surgical environment and/or a robotic surgical procedure performed therein. For example, the one or more sensors 750 in the robotic surgical environment may be configured to detect a status of a robotic component corresponding to a virtual robotic component in the virtual robotic surgical environment (e.g., the virtual robotic component may be substantially representative of the robotic component in visual form and/or function). In this variation, the virtual reality processor 210 may be configured to receive the detected status of the robotic component, and then modify the virtual robotic component based at least in part on the detected status such that the virtual robotic component mimics the robotic component. For example, if a surgeon moves a robotic arm during a robotic surgical procedure to a particular pose, then a virtual robotic arm in the virtual environment may move correspondingly.

As another example, the virtual reality processor 210 may receive status information indicating an alarm event, such as an impending or present collision between objects, or poor patient health condition. Upon receiving such information, the virtual reality processor 210 may provide a warning or alarm to the user of the occurrence of the event, such as by displaying a visual alert (e.g., text, icon indicating collision, a view within the virtual environment depicting the collision, etc.), audio alert, etc.

As yet another example, the one or more sensors in the robotic surgical environment may be used to compare an actual surgical procedure (occurring in the non-virtual robotic surgical environment) with a planned surgical procedure as planned in a virtual robotic surgical environment. For example, an expected position of at least one robotic component (e.g., robotic arm) may be determined during surgical preplanning, as visualized as a corresponding virtual robotic component in a virtual robotic surgical environment. During an actual surgical procedure, one or more sensors may provide information about a measured position of the actual robotic component. Any differences between the expected and measured position of the robotic component may indicate deviations from a surgical plan that was constructed in the virtual reality environment. Since such deviations may eventually result in undesired consequences (e.g., unintended collisions between robotic arms, etc.), identification of deviations may allow the user to adjust the surgical plan accordingly (e.g., reconfigure approach to a surgical site, change surgical instruments, etc.).

User Modes

Generally, the virtual reality system may include one or more user modes enabling a user to interact with the virtual robotic surgical environment by moving and/or manipulating the handheld controllers 230. Such interactions may include, for example, moving virtual objects (e.g., virtual robotic arm, virtual tool, etc.) in the virtual environment, adding camera viewpoints to view the virtual environment simultaneously from multiple vantage points, navigate within the virtual environment without requiring the user to move the head-mounted display 220 (e.g., by walking), etc. as further described below.

Figure 8:
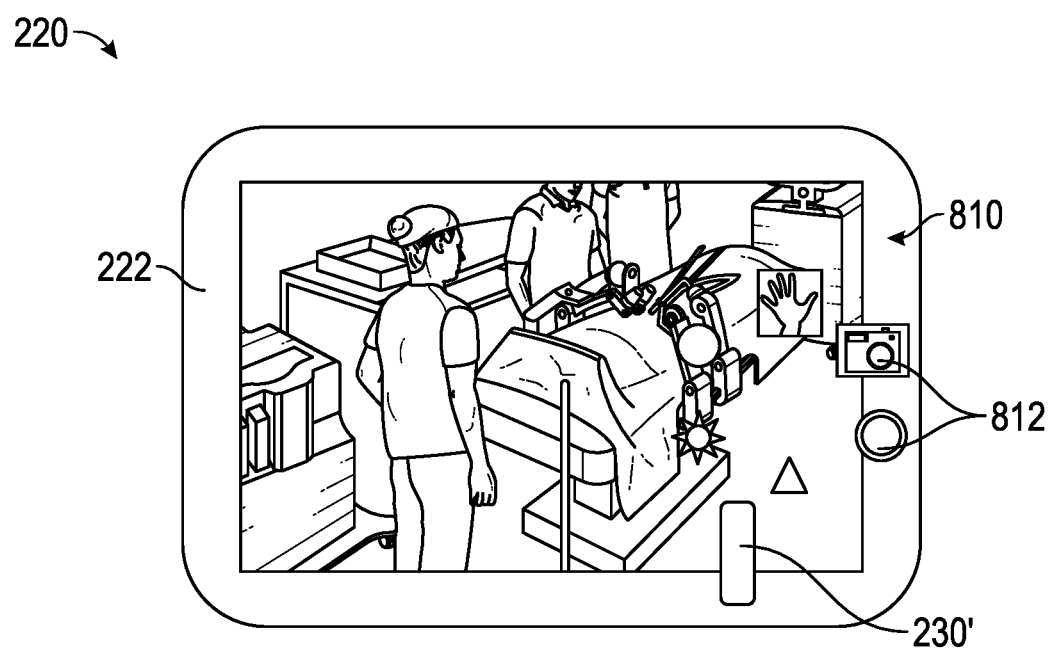
FIG. 8 is a schematic illustration of a displayed menu for selecting one or more user modes of one variation of a virtual reality system.

In some variations, the virtual reality system may include a plurality of user modes, where each user mode is associated with a respective subset of user interactions. As shown in FIG. 8, at least some of the user modes may be shown on a display (e.g., head-mounted display 220) for user selection. For example, at least some of the user modes may correspond to selectable user mode icons 812 displayed in a user mode menu 810. The user mode menu 810 may be overlaid on the display of the virtual robotic surgical environment such that a graphical representation 230' of the handheld controller (or user hand, other suitable representative icon, etc.) may be maneuvered by the user to select a user mode icon, thereby activating the user mode corresponding to the selected user mode icon. As shown in FIG. 8, the user mode icons 812 may be generally arranged in a palette or circle, but may be alternatively arranged in a grid or other suitable arrangement. In some variations, a selected subset of possible user modes may be presented in the menu 810 based on, for example, user preferences (e.g., associated with a set of user login information), preferences of users similar to the current user, type of surgical procedure, etc.

Figure 14:
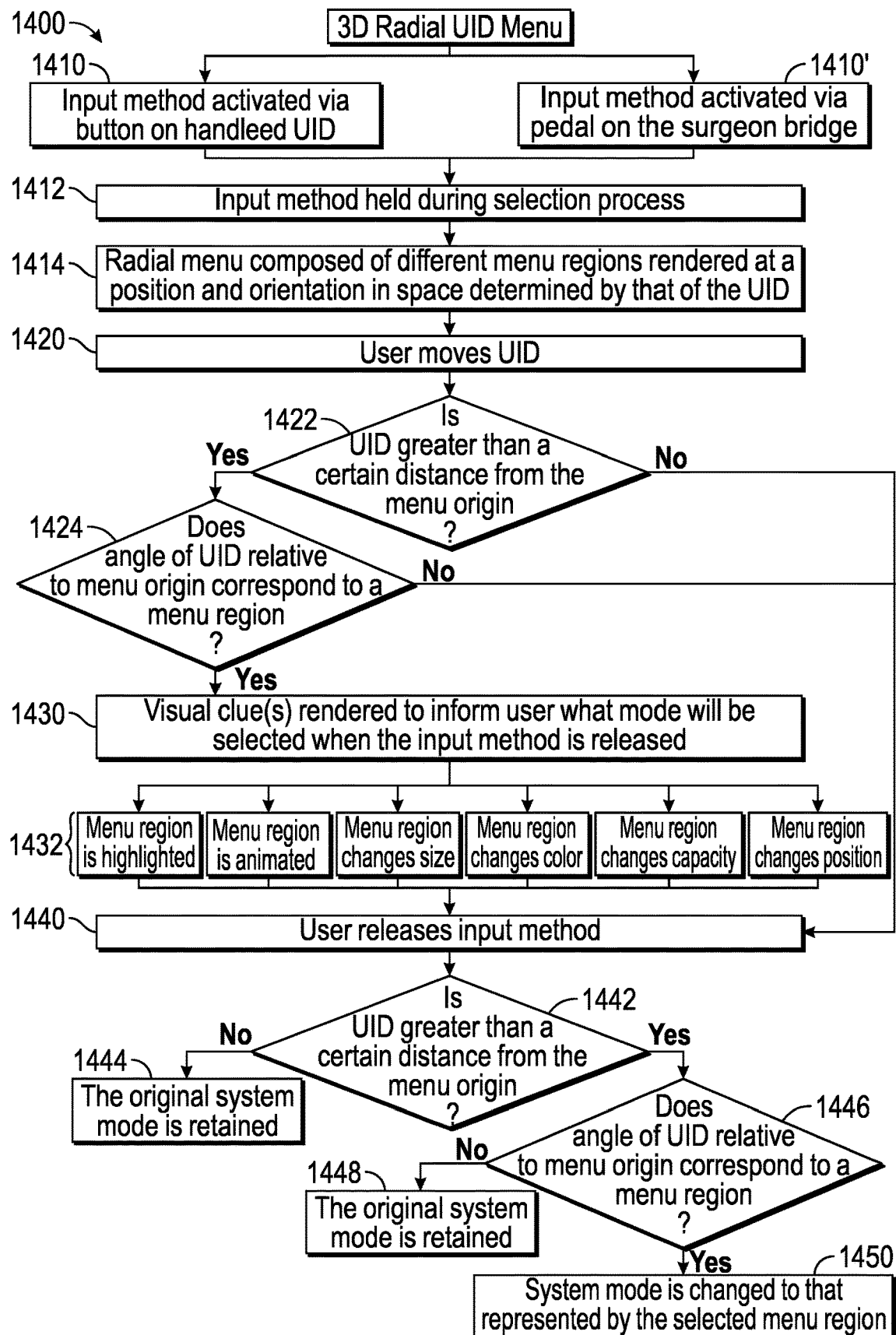
FIG. 14 is a flowchart of an exemplary variation of a method for operating a user mode menu for selection of user modes in a virtual reality system.

FIG. 14 illustrates a method of operation 1400 of an exemplary variation of a user mode menu providing selection of one or more user mode icons. To activate the user menu, the user may activate a user input method associated with the menu. For example, an input method may be activated by a user engaging with a handheld controller (e.g., handheld user interface device), such as by pressing a button or other suitable feature on the handheld controller (1410). As another example, an input method may be activated by a user engaging a pedal or other feature of a user console (1410'). Voice commands and/or other devices may additionally or alternatively be used to activate an input method associated with the menu. While the input method is engaged (1412), the virtual reality system may render and display an array of user mode icons (e.g., arranged in a palette around a central origin as shown in FIG. 8A). The array of user mode icons may be generally displayed near or around a graphical representation of the handheld controller and/or at a rendered cursor that is controlled by the handheld controller.

For example, in one variation in which a handheld controller includes a circular menu button and a graphical representation of the handheld controller also has a circular menu button displayed in the virtual reality environment, the array of user mode icons may be centered around and aligned with the menu button such that the normal vectors of the menu plane and menu button are substantially aligned. The circular or radial menu may include, for example, multiple different menu regions (1414) or sectors, each of which may be associated with an angle range (e.g., an arcuate segment of the circular menu) and a user mode icon (e.g., as shown in FIG. 8). Each region may be toggled between a selected state and an unselected state.

The method 1400 may generally include determining selection of a user mode by the user and receiving confirmation that the user would like to activate the selected user mode for the virtual reality system. To select a user mode in the user mode menu, the user may move the handheld controller (1420) to freely manipulate the graphical representation of the handheld controller and navigate through the user mode icons in the user mode menu. Generally, the position/orientation of the handheld controller (and position/orientation of the graphical representation of the handheld controller which moves in correspondence with the handheld controller) may be analyzed to determine whether the user has selected a particular user mode icon. For example, in variations in which the user mode icons are arranged in a generally circular palette around a central origin, the method may include determining radial distance and/or angular orientation of the graphical representation of the handheld controller relative to the central origin. For example, a test for determining user selection of a user mode icon may include one or more prongs, which may be satisfied in any suitable order. In a first prong (1422), the distance of the graphical representation of the handheld controller to the center of the user mode menu (or another reference point in the user mode menu) is compared to a distance threshold. The distance may be expressed in terms of absolute distance (e.g., number of pixels) or ratios (e.g., percentage of distance between a center point and the user mode icons arranged around the periphery of the user mode menu, such as 80% or more). If the distance is less than the threshold, then it may be determined that no user mode icon is selected. Additionally or alternatively, selection of a user mode icon may depend on a second prong (1424). In the second prong (1424), the orientation of the graphical representation of the handheld controller is measured and correlated to a user mode icon associated with an arcuate segment of the menu. If the orientation corresponds to a selected arcuate segment of the menu, then it may be determined that a particular user mode (associated with the selected arcuate segment) is selected by the user. For example, a user mode icon may be determined as selected by the user if both the distance and the angular orientation of the graphical representation of the handheld controller relative to the origin satisfy the conditions (1422) and (1424).

After determining that a user has selected a particular user mode icon, the method may, in some variations, convey such selection to the user (e.g., as confirmation) by visual and/or auditory indications. For example, in some variations, the method may include rendering one or more visual cues (1430) in the displayed virtual reality environment in response to determining that a user has selected a user mode icon. As shown in FIG. 14, exemplary visual cues (1432) include modifying the appearance of the selected user mode icon (and/or the arcuate segment associated with the selected user mode icon) with highlighting (e.g., thickened outlines), animation (e.g., wiggling lines, "dancing" or "pulsating" icon), change in size (e.g., enlargement of icon), change in apparent depth, change in color or opacity (e.g., more or less translucent, change in pattern fill of icon), change in position (e.g., move radially outward or inward from the central origin, etc.), and/or any suitable visual modification. In some variations, indicating to the user in these or any suitable manner may inform the user which user mode will be activated, prior to the user confirming the selection of a particular user mode. For example, the method may include rendering one or more visual cues (1430) as the user navigates or scrolls through the various user mode icons in the menu.

The user may confirm approval of the selected user mode icon in one or more various manners. For example, the user may release or deactivate the user input method (1440) associated with the menu (e.g., releasing a button on the handheld controller, disengaging a foot pedal), such as to indicate approval of the selected user mode. In other variations, the user may confirm selection by hovering over the selected user mode icon for at least a predetermined period of time (e.g., at least 5 seconds), double-clicking the user input method associated with the user menu (e.g., double-clicking the button, etc.), speaking a verbal command indicating approval, etc.

In some variation, upon receiving confirmation that the user approves the selected user mode, the mothed may include verifying which user mode icon has been selected. For example, as shown in FIG. 14, a test for verifying which user mode icon has been selected may include one or more prongs, which may be satisfied in any suitable order. For example, in variations in which the user mode icons are arranged in a generally circular palette around a central origin, the method may include determining radial distance relative to the central origin (1442) and/or angular orientation of the graphical representation of the handheld controller relative to the central origin (1446) when the user indicates approval of user mode icon selection. In some variations, prongs (1442) and (1446) may be similar to prongs (1422) and (1424) described above, respectively. If at least one of these prongs (1442) and (1444) is not satisfied, then the release of the user input method may correlate to a non-selection of a user mode icon (e.g., the user may have changed his or her mind about selecting a new user mode). Accordingly, if the graphical representation of the handheld controller fails to satisfy the distance threshold (1442) then the original or previous user mode may be retained (1444).

Similarly, if the graphical representation of the handheld controller fails to correspond to an arcuate segment of the menu (1446), then the original or previous user mode may be retained (1448). If the graphical representation of the handheld controller does satisfy the distance threshold (1442) and corresponds to an arcuate segment of the menu, then the selected user mode may be activated (1450). In other variations, a user mode may additionally or alternatively be selected with other interactions, such as voice command, eye-tracking via sensors, etc. Furthermore, the system may additionally or alternatively suggest activation of one or more user modes based on criteria such as user activity within the (e.g., if the user is frequently turning his head to see detail on the edge of his field of view, the system may suggest a user mode enabling placement of a camera to provide a heads-up display window view from a desired vantage point, as described below), type of surgical procedure, etc.

One exemplary user mode with the virtual robotic surgical environment enables a user to grip, move, or otherwise manipulate virtual objects in the virtual environment. Examples of manipulable virtual objects include, but are not limited to, virtual representations of physical items (e.g., one or more virtual robotic arms, one or more virtual tool drivers, virtual manual laparoscopic tools, virtual patient operating table or other resting surface, virtual control tower or other equipment, virtual user console, etc.) and other virtual or graphical constructs such as portals, window display, patient imaging or other projections on a heads-up display, etc. which are further described below.

Object Gripping

At least some of the virtual objects may include or be associated with at least one virtual touchpoint or selectable feature. When the virtual touchpoint is selected by a user, the user may move (e.g., adjust position and/or orientation) the virtual object associated with the selected virtual touchpoint. Furthermore, multiple virtual touchpoints may be simultaneously selected (e.g., with multiple handheld controllers 230 and their graphical representations 230') on the same virtual object or multiple separate virtual objects.

The user may generally select a virtual touchpoint by moving a handheld controller 230 to correspondingly move a graphical representation 230' to the virtual touchpoint in the virtual environment, then engaging an interactive feature such as a trigger or button on the handheld controller 230 to indicate selection of the virtual touchpoint. In some variations, a virtual touchpoint may remain selected as long as the user engages the interactive feature on the handheld controller 230 (e.g., as long as the user depresses a trigger) and may become unselected when the user releases the interactive feature. For example, the virtual touchpoint may enable the user to "click and drag" the virtual object via the virtual touchpoint. In some variations, a virtual touchpoint may be toggled between a selected state and an unselected state, in that a virtual touchpoint may remain selected after a single engagement of the interactive feature on the handheld controller until a second engagement of the interactive feature toggles the virtual touchpoint to an unselected state. In the virtual robotic surgical environment, one or both kinds of virtual touchpoints may be present.

A virtual object may include at least one virtual touchpoint for direct manipulation of the virtual object. For example, a virtual robotic arm in the virtual environment may include a virtual touchpoint on one of its virtual arm links. The user may move a handheld controller 230 until the graphical representation 230' of the handheld controller is in proximity to (e.g., hovering over) the virtual touchpoint, engage a trigger or other interactive feature on the handheld controller 230 to select the virtual touchpoint, then move the handheld controller 230 to manipulate the virtual robotic arm via the virtual touchpoint. Accordingly, the user may manipulate the handheld controller 230 in order to reposition the virtual robotic arm in a new pose, such as to create a more spacious workspace in the virtual environment by the patient, test range of motion of the virtual robotic arm to determine likelihood of collisions between the virtual robotic arm and other objects, etc.

A virtual object may include at least one virtual touchpoint that is associated with a second virtual object, for indirect manipulation of the second virtual object. For example, a virtual control panel may include a virtual touchpoint on a virtual switch or button that is associated with a patient operating table. The virtual switch or button may, for example, control the height or angle of the virtual patient operating table in the virtual environment, similar to how a switch or button on a real control panel might electronically or mechanically modify the height or angle of a real patient operating table. The user may move a handheld controller 230 until the graphical representation 230' of the handheld controller is in proximity to (e.g., hovering over) the virtual touchpoint, engage a trigger or other interactive feature on the handheld controller 230 to select the virtual touchpoint, then move the handheld controller 230 to manipulate the virtual switch or button via the virtual touchpoint. Accordingly, the user may manipulate the handheld controller 230 in order to modify the height or angle of the virtual environment, such as to improve angle of approach or access to a workspace in the virtual environment.

When a virtual touchpoint is selected, the virtual reality processor may modify the virtual robotic surgical environment to indicate to the user that the virtual touchpoint is indeed selected. For example, the virtual object including the virtual touchpoint may be highlighted by being graphically rendered in a different color (e.g., blue or red) and/or outlined in a different line weight or color, in order to visually contrast the affected virtual object from other virtual objects in the virtual environment. Additionally or alternatively, the virtual reality processor may provide audio feedback (e.g., a tone, beep, or verbal acknowledgment) through an audio device indicating selection of the virtual touchpoint, and/or tactile feedback (e.g., a vibration) through a handheld controller 230, the head-mounted display 220, or other suitable device.

Navigation

Other exemplary user modes with the virtual robotic surgical environment may enable a user to navigate and explore the virtual space within the virtual environment.

Snap Points

In some variations, the system may include a user mode enabling "snap points", or virtual targets within a virtual environment which may be used to aid user navigation within the virtual environment. A snap point may, for example, be placed at a user-selected or default location within the virtual environment and enable a user to quickly navigate to that location upon selection of the snap point. A snap point may, in some variations, be associated with an orientation within the virtual environment and/or an apparent scale (zoom level) of the display of the environment from that vantage point. Snap points may, for example, be visually indicated as colored dots or other colored markers graphically displayed in the first-person perspective view.

By selecting a snap point, the user may be transported to the vantage point of the selected snap point within the virtual robotic surgical environment.

Figure 16:
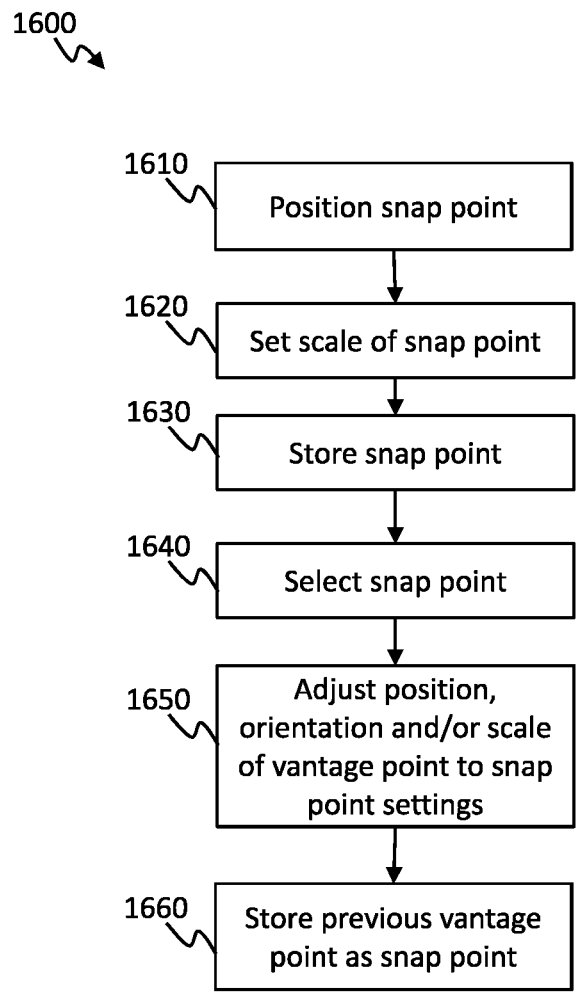
FIG. 16 is a flowchart of an exemplary variation of a method for operating a user mode enabling snap points in a virtual environment.

For example, FIG. 16 illustrates method of operation 1600 of an exemplary variation of a user mode enabling snap points. As shown in FIG. 16, a snap point may be positioned (1610) in the virtual environment by a user or as a predetermined setting. For example, a user may navigate through a user mode menu as described above, and select or "grab" a snap point icon from the menu with a handheld controller (e.g., indicated with a colored dot or other suitable marker) and drag and drop the snap point icon to a desired location and/or orientation in the virtual environment. The snap point may, in some variations, be repositioned by the user reselecting the snap point (e.g., moving the graphical representation of the handheld controller until it intersects with the snap point or a collision volume boundary around the snap point, then engaging an input feature such as a button or trigger) and dragging and dropping the snap point icon to a new desired location. In some variations, the user may set the scale or zoom level of the vantage point (1620) associated with the snap point, such by adjusting a displayed slider bar or scroll wheel, motions as described above for setting a scale level for an environmental view manipulation, etc. The snap point may, in some examples, have a default scale level associated with all or a subcategory of snap points, a scale level associated with the current vantage point of the user when the user places the snap point, or adjusted as described above. Furthermore, once a snap point is placed, the snap point may be stored (1630) in memory (e.g., local or remote storage) for future access. A snap point may, in some variations, be deleted from the virtual environment and from memory. For example, a snap point may be selected (in a similar manner as for repositioning of the snap point) and designed for deletion by dragging it off-screen to a predetermined location (e.g., virtual trash can) and/or moving it with a predetermined velocity (e.g., "thrown" in a direction away from the user's vantage point with a speed greater than a predetermined threshold), selection of a secondary menu option, voice command, etc.

Once one or more snap points for a virtual environment are stored in memory, the user may select one of the stored snap points (1640) for use. For example, upon selection of a stored snap point, the user's vantage point may be adjusted to the position, orientation, and/or scale of the selected snap point's settings (1650), thereby allowing the user to feel as if they are teleporting to the location associated with the selected snap point. In some variations, the user's previous vantage point may be stored as a snap point (1660) to enable easy "undo" of the user's perceived teleportation and transition the user back to their previous vantage point. Such a snap point may be temporary (e.g., disappear after a predetermined period of time, such as after 5-10 seconds). In some examples, the user's previous vantage point may be stored as a snap point only if the user's previous location was not a pre-existing snap point. Furthermore, in some variations, a virtual trail or trajectory (e.g., line or arc) may be displayed in the virtual environment connecting the user's previous vantage point to the user's new vantage point associated with the selected snap point, which may, for example, provide the user with context as to how they have teleported within the virtual environment. Such a visual indication may be removed from the display of the virtual environment after a predetermined period of time (e.g., after 5-10 seconds).

Generally, in some variations, a snap point may operate in a similar manner as portals described below, except that a snap point may indicate a vantage point without providing a window preview of the virtual environment. For example, snap points may be placed at user-selected vantage points outside and/or inside the virtual patient, and may be linked into one or more trajectories, similar to portals as described above. In some variations, snap point trajectories may be set by the user in a manner similar to that described below for portals.

Portals

In some variations, the system may include a user mode that facilitates placement of one or more portals, or teleportation points, at user-selected locations in the virtual environment. Each portal may, for example, serve as a transportation gateway to a corresponding vantage point in the virtual environment, thereby allowing the user to swiftly change vantage points for viewing and navigating the virtual environment. Generally, upon selection (e.g., with one or more handheld controllers 230) of a portal, the user's apparent location may transition to the location of the selected portal, such that the user views the virtual environment from the selected portal's vantage point and has the sensation of "jumping" around the virtual environment. By placing one or more portals around the virtual environment, the user may have the ability to quickly move between various vantage points. Placement, adjustment, storing, and/or navigation of portals around the virtual environment may be similar to that of snap points described above.

Figure 9A:
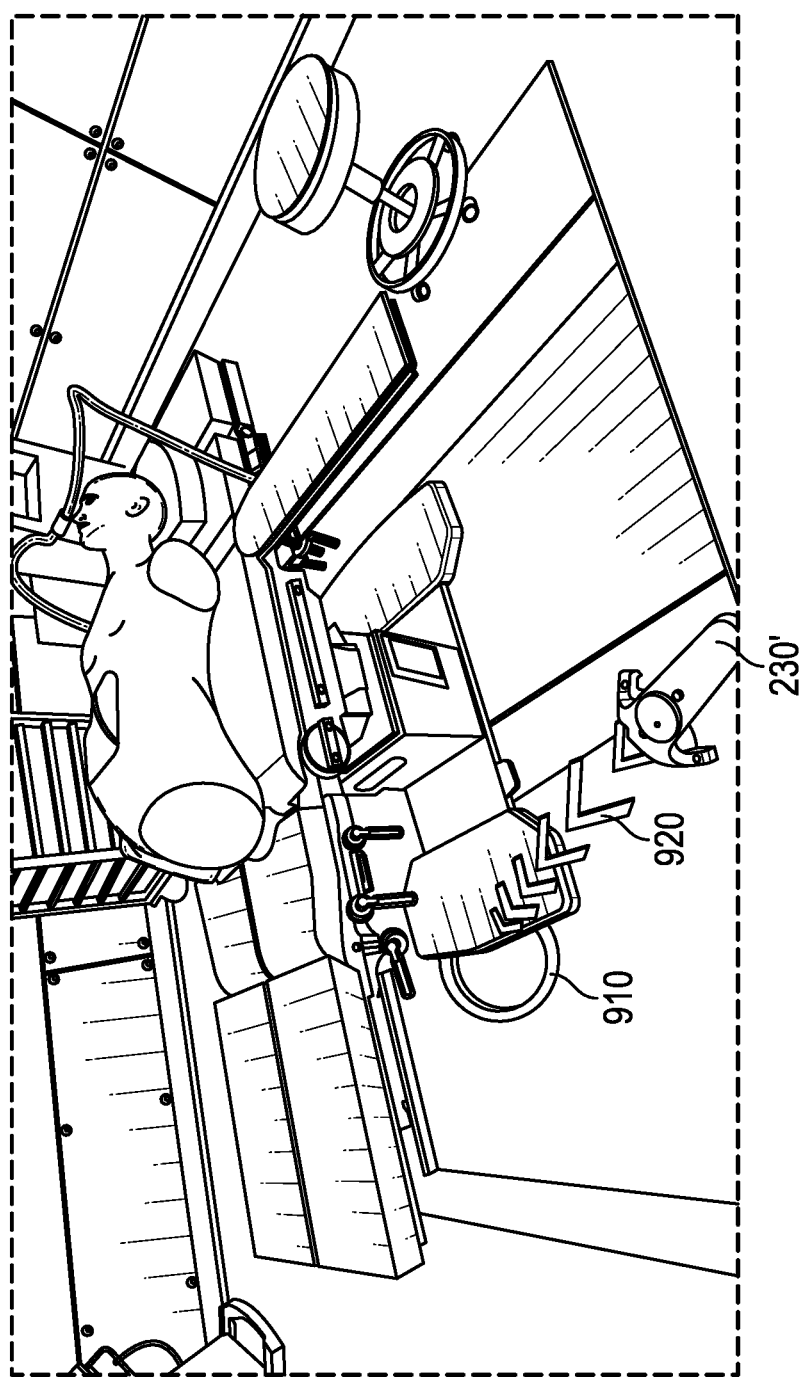
FIGS. 9A-9C are schematic illustrations of a virtual robotic surgical environment with exemplary portals.

For example, as generally described above, the system may display a first-person perspective view of the virtual robotic surgical environment from a first vantage point within the virtual robotic surgical environment. The user may navigate through a menu to select a user mode that enables placement of a portal. As shown in FIG. 9A, the user may manipulate the graphical representation 230' of the handheld controller to position a portal 910 in a selected location in the virtual environment. For example, the user may engage a feature (e.g., trigger or button) on the handheld controller while a portal placement-enabling user mode is activated, such that while the feature is engaged and the user moves the position and/or orientation of the handheld controller, a portal 910 may appear and be moved within the virtual environment. One or more portal placement indicators 920 (e.g., one or more arrows, a line, an arc, etc. connecting the graphical representation 230' to a prospective portal location) may aid in communicating to the user the prospective location of a portal 910, such as by helping with depth perception. Size of the portal 910 may be adjusted by "grabbing" and stretching or shrinking the sides of the portal 910 via the handheld controllers. When the portal 910 location is confirmed (e.g., by the user releasing the engaged feature on the handheld controller, double-clicking, etc.), the user's apparent location within the virtual environment may be updated to match the vantage point associated with the portal 910. In some variations, as described below, at least some vantage points within the virtual location may be prohibited. These prohibited vantage points may be stored in memory (e.g., local or remote storage). In these variations, if a portal 910 location is confirmed in a prohibited location (e.g., compared to and matched among a list of prohibited vantage points stored in memory), then the user's apparent location within the virtual environment may be retained with no changes. However, if a portal 910 location is confirmed as permissible (e.g., compared to and not matched among the list of prohibited vantage points), then the user's apparent location within the virtual environment may be updated as described above.

In some variations, once the user has placed the portal 910 at a desired vantage point, a window view of the virtual environment from the vantage point of the placed portal 910 may be displayed within the portal 910, thereby offering a "preview" of the view offered by the portal 910. The user may, for example, view through the portal 910 with full parallax, such that the portal 910 behaves as a type of magnifying lens. For example, while looking through the portal 910, the user may view the virtual environment as if the user has been scaled to the inverse of the portal's scale factor (which affects both the interpupillary distance and the focal distance) and as if the user has been translated to the reciprocal of the portal's scale factor (1/portal scale factor) of the distance from the portal 910 to the user's current location. Furthermore, the portal 910 may include an "event horizon" which may be a texture on a plane that is rendered, for example, using additional one or more cameras (described below) within the virtual environment scene positioned as described above. In these variations, when "traveling" through the portal 910 after selecting the portal 910 for teleportation, the user's view of the virtual environment may naturally converge with the user's apparent vantage point during the user's approach to the portal, since the user's vantage point is offset as a fraction of the distance from the portal (by 1/portal scale factor). Accordingly, the user may feel as if they are smoothly and naturally stepping into viewing the virtual environment at the scale factor associated with the selected portal.

As shown in FIG. 9A, in some variations, the portal 910 may be generally circular. However, in other variations, one or more portals 910 may be any suitable shape, such as elliptical, square, rectangular, irregular, etc. Furthermore, the window view of the virtual environment that is displayed in the portal may display the virtual environment at a scale factor associated with the portal, such that the view of the virtual environment displayed in different portals may be displayed at different "zoom" levels (e.g., 1×, 1.5×, 2×, 2.5×, 3×, etc.), thereby also changing the scale of the user relative to the environment. The scale factor of the window view in a portal may also indicate or correspond with the scale of the view that would be displayed if the user is transported to that portal's vantage point. For example, if a view of the virtual environment outside a virtual patient is about 1×, then a window view of the virtual environment inside the virtual patient may be about 2× or more, thereby providing a user with more detail of the internal tissue of the virtual patient. The scale factor may be user-defined or predetermined by the system (e.g., based on location of the portal in the virtual environment). In some variations, the scale factor may correlate to the displayed size of the portal 910, though in other variations, the scale factor may be independent of the portal size.

Figure 9B:
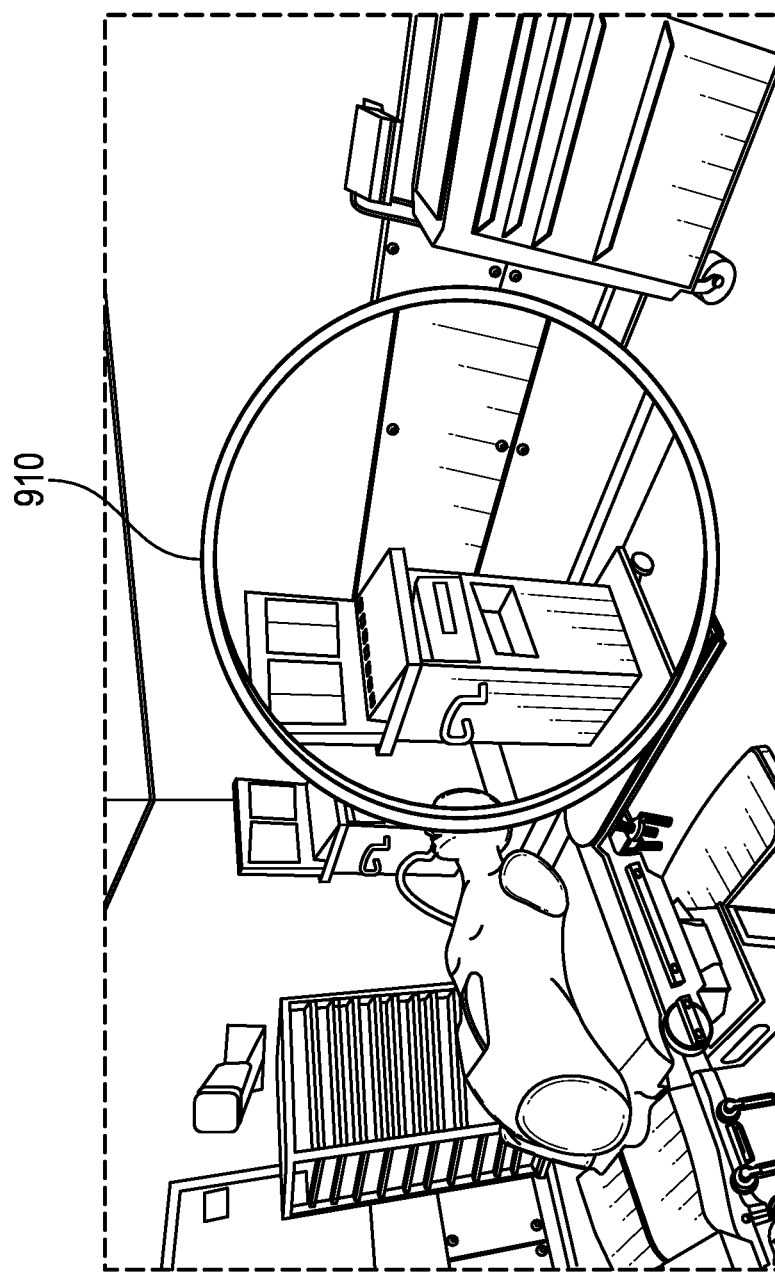
Figure 9C:
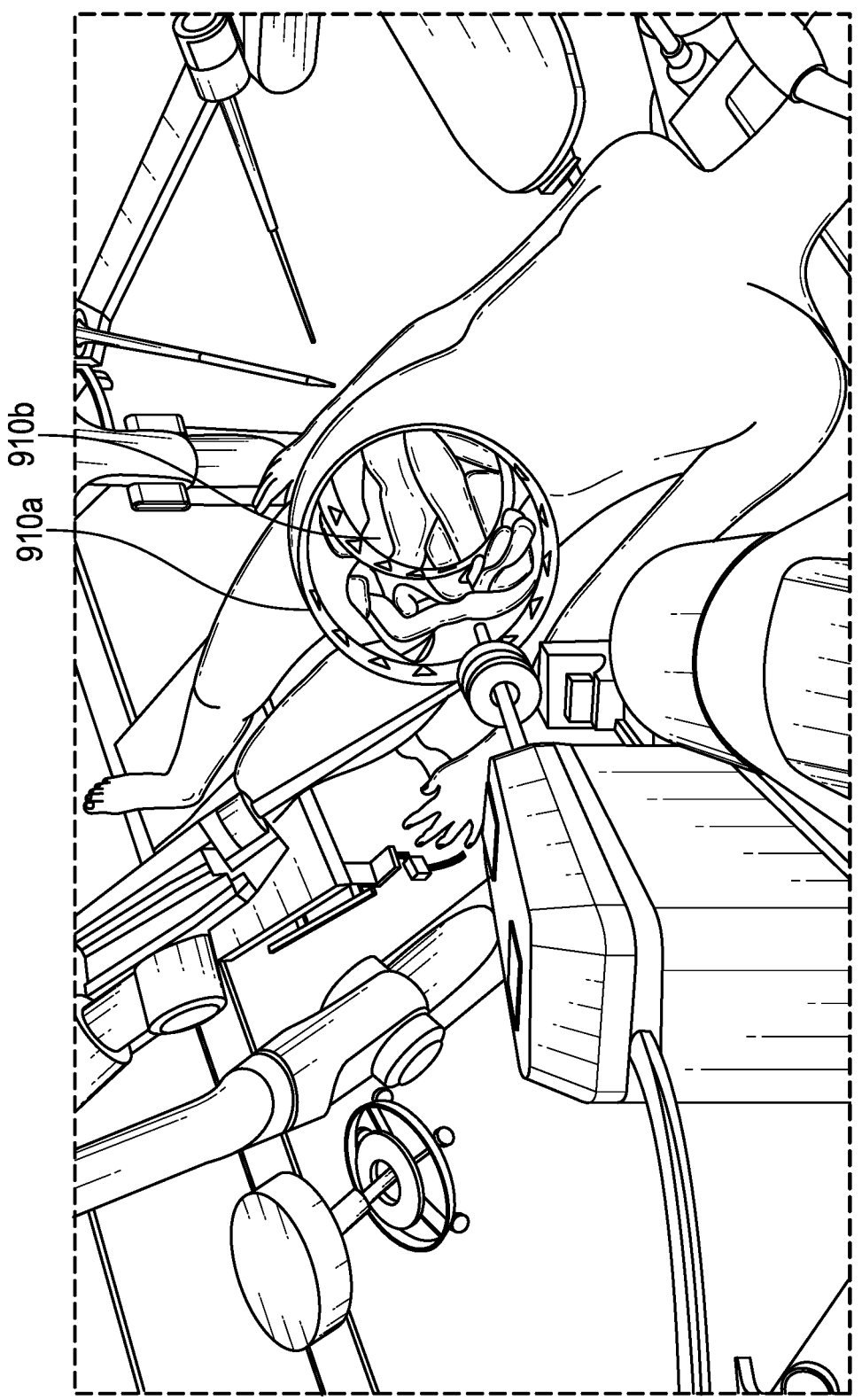

In some variations, a portal 910 may be placed in substantially any vantage point in the virtual environment that the user desires. For example, a portal 910 may be placed anywhere on a virtual ground surface of the virtual operating room or on a virtual object (e.g., table, chair, user console, etc.). As another example, as shown in FIG. 9B, a portal 910 may be placed in mid-air at any suitable elevation above the virtual ground surface. As yet another example, as shown in FIG. 9C, a portal may be placed on or inside a virtual patient, such as portals 910a and 910b which are placed on the abdomen of a patient and enable views of the intestines and other internal organs of the virtual patient (e.g., simulated augmented reality). In this example, the virtual patient may be generated from medical imaging and other information for a real (non-virtual) patient, such that portals 910a and 910b may enable the user to have an immersive view of an accurate representation of the real patient's tissue (e.g., for viewing tumors, etc.), and/or generated from internal virtual cameras (described below) placed inside the patient. In some variations, the system may limit placement of a portal 910 according to predefined guidelines (e.g., only outside the patient or only inside the patient), which may correspond, for example, to a type of simulated surgical procedure or a training level (e.g., "beginner" or "advanced" user level) associated with the virtual environment. Such prohibited locations may be indicated to the user by, for example, a visual change in the portal 910 as it is being placed (e.g., changing outline color, displaying a grayed-out or opaque window view within the port 910 as it is being placed) and/or auditory indications (e.g., beep, tone, verbal feedback). In yet other variations, the system may additionally or alternatively include one or more portals 910 placed in predetermined locations, such as at a virtual user console in the virtual environment, adjacent the virtual patient table, etc. Such predetermined locations may, for example, depend on the type of procedure, or be saved as part of a configuration file.

A portal 910 may be viewable from either "side" (e.g., front side and rear side) of the portal. In some variations, the view from one side of the portal 910 may be different from an opposite side of the portal 910. For example, when viewed from a first side (e.g., front) of the portal 910, the portal may provide a view of the virtual environment with a scale factor and parallax effects as described above, while when viewed from a second side (e.g., rear) of the portal 910, the portal may provide a view of the virtual environment with a scale factor of about one. As another example, the portal may provide a view of the virtual environment with a scale factor and parallax effects when viewed from both the first side and the second side of the portal.

In some variations, multiple portals 910 may be sequentially linked to include a trajectory in the virtual environment. For example, as shown in FIG. 9C, a first-person perspective view of the virtual robotic surgical environment from a first vantage point may be displayed (e.g., an immersive view). The user may place a first portal 910a in a second vantage point that is different from the first vantage point (e.g., closer to the virtual patient than the first vantage point) and a first window view of the virtual robotic surgical environment from the second vantage point may be displayed in the first portal 910a. Similarly, the user may place a second portal 910b in a third vantage point (e.g., closer to the patient than the first and second vantage points), and a second window view of the virtual robotic surgical environment may be displayed in the second portal 910b. The user may provide a user input associating the first and second portals 910a and 910b (e.g., by selection with the handheld controllers, drawing a line between the first and second portals with the handheld controllers, etc.) such that the first and second portals are sequentially linked, thereby generating a trajectory between the first and second portals.

In some variations, after multiple portals 910 are linked to generate a trajectory, transportation along the trajectory may not require explicit selection of each sequential portal. For example, once on the trajectory (e.g., at the second vantage point), traveling between linked portals may be accomplished by engagement of a trigger, button, touchpad, scroll wheel, other interactive feature of the handheld controller, voice command, etc.

Additional portals may be linked in a similar manner. For example, two, three, or more portals may be linked in series to generate an extended trajectory. As another example, multiple portals may form "branched" trajectories, where at least two trajectories share at least one portal in common but otherwise each trajectory has at least one portal that is unique to that trajectory. As yet another example, multiple portals may form two or more trajectories that share no portals in common. The user may select which trajectory on which to travel, such as by using the handheld controllers and/or voice command, etc. One or more trajectories between portals may be visually indicated (e.g., with a dotted line, color coding of portals along the same trajectory, etc.), and such visual indication of trajectories may be toggled on and off, such as based on user preference.

Other portal features may facilitate easy navigation of the trajectories between portals. For example, a portal may change color when the user has entered and gone through that portal. As shown in FIG. 9C, in another example, a portal itself may be displayed with direction arrows indicating the permissible direction of the trajectory including that portal. Furthermore, travel along the trajectories may be accomplished with an "undo" command (via handheld controllers and/or voice command, etc.) that returns the user to the previous vantage point (e.g., displays the view of the virtual environment from the previous vantage point). In some variations, a home or default vantage point may be established (such as according to user preference or system settings) in order to enable a user to return to that home vantage point quickly with a shortcut command, such as an interactive feature on a handheld controller or a voice command (e.g., "Reset my position"). For example, a home or default vantage point may be at a virtual user console or adjacent to the virtual patient table.

The user mode facilitating placement and use of portals, or another separate user mode, may further facilitate deletion of one or more portals. For example, a portal may be selected for deletion with the handheld controllers. As another example, one or more portals may be selected for deletion via voice command (e.g., "delete all portals" or "delete portal A").

Free Navigation

The system may include a user mode that facilitates free navigation around the virtual robotic surgical environment. For example, as described herein, the system may be configured to detect the user's walking movements based on sensors in the head-mounted display and/or handheld controllers, and may correlate the user's movements into repositioning within a virtual operating room.

In another variation, the system may include a flight mode that enables the user to quickly navigate the virtual environment in a "flying" manner at different elevations and/or speeds, and at different angles. For example, the user may navigate in flight mode by directing one or more handheld controllers and/or the headset in a desired direction for flight. Interactive features on the handheld controller may further control flight. For example, a directional pad or touchpad may provide control for forward, backward, strafing, etc. motions while maintaining substantially the same perspective view of the virtual environment. Translation may, in some variations, occur without acceleration, as acceleration may tend to increase the likelihood of simulator sickness. In another user setting, a directional pad or touchpad (or orientation of the headset) may provide control for elevation of the user's apparent location within the virtual environment. Furthermore, in some variations, similar to that described above with respect to portals, a home or default vantage point within the flight mode may be established in order to enable a user to return to that home vantage point quickly with a shortcut command. Parameters such as speed of flight in response to a user input may be adjustable by the user and/or set by the system by default.

Figure 10A:
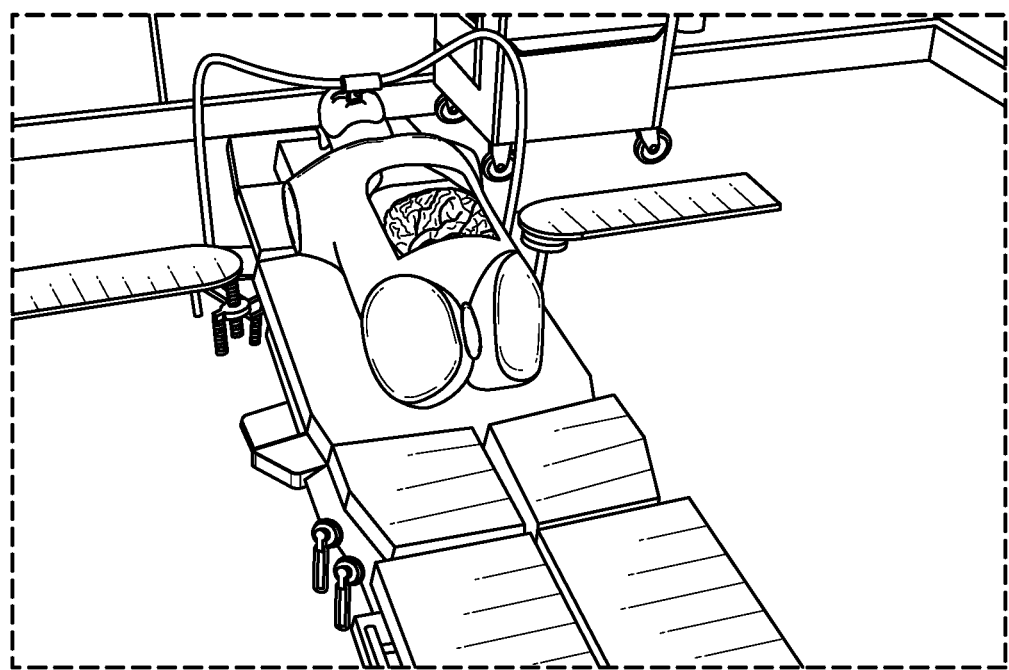
FIGS. 10A and 10B are schematic illustrations of an exemplary virtual robotic surgical environment viewed in a flight mode.
Figure 10B:
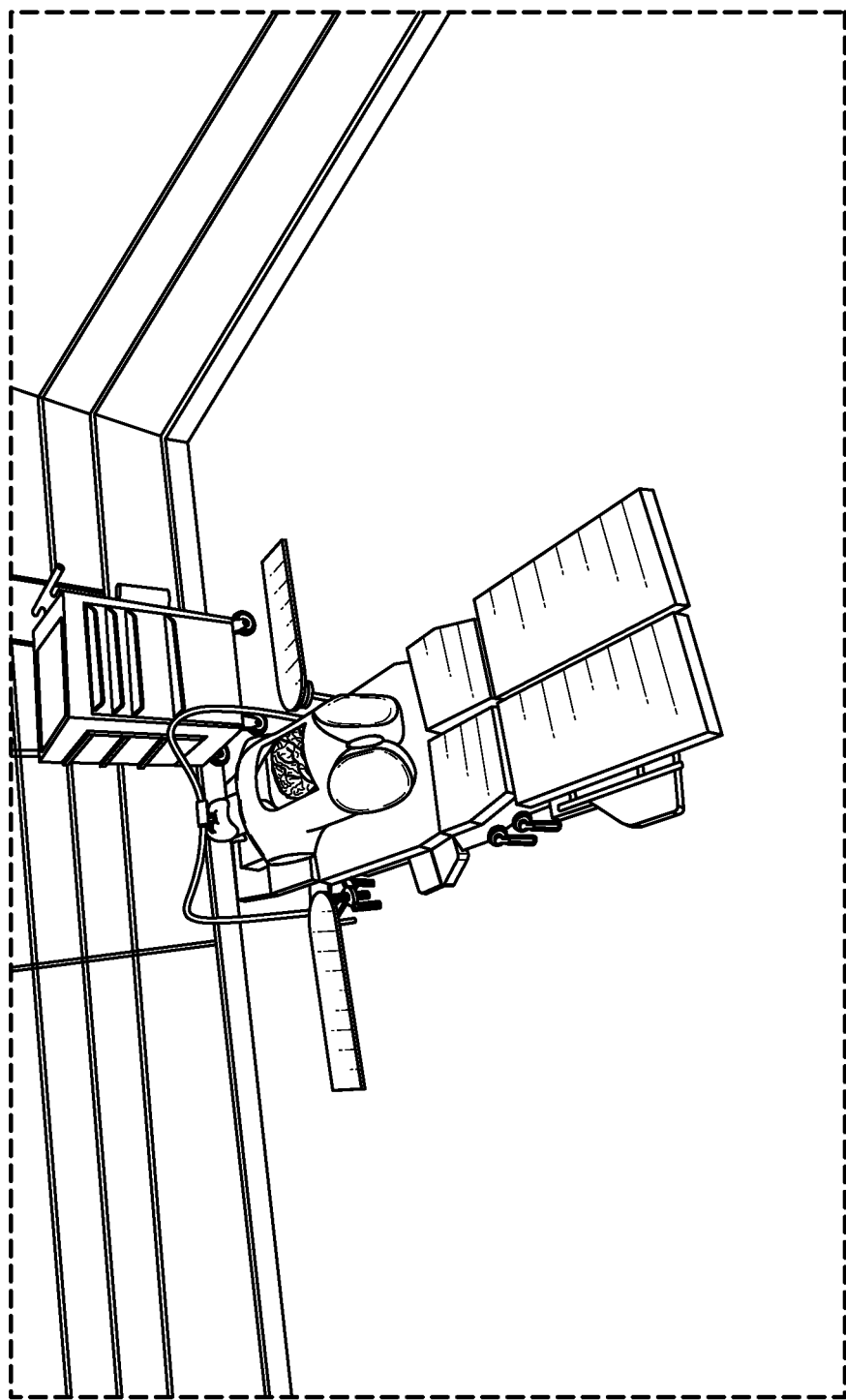

Furthermore, in flight mode, the scaling factor of the displayed view may be controlled via the handheld controllers. The scaling factor may, for example, affect apparent elevation of the user's location within the virtual environment. In some variations, the user may use the handheld controllers to pull apart two points in the displayed view to zoom out and draw closer two points in the displayed view to zoom in, or conversely pull apart two points in the displayed view to zoom in and draw closer two points in the displayed view to zoom out. Additionally or alternatively, the user may utilize voice commands (e.g., "increase zoom to 2×") to change the scaling factor of the displayed view. For example, FIGS. 10A and 10B illustrate exemplary views of the virtual environment that are relatively "zoomed in" and "zoomed out," respectively. Parameters such as the speed of the change in scaling factor, minimum and maximum scaling factor ranges, etc. may be adjustable by the user and/or set by the system by default.

Figure 10C:
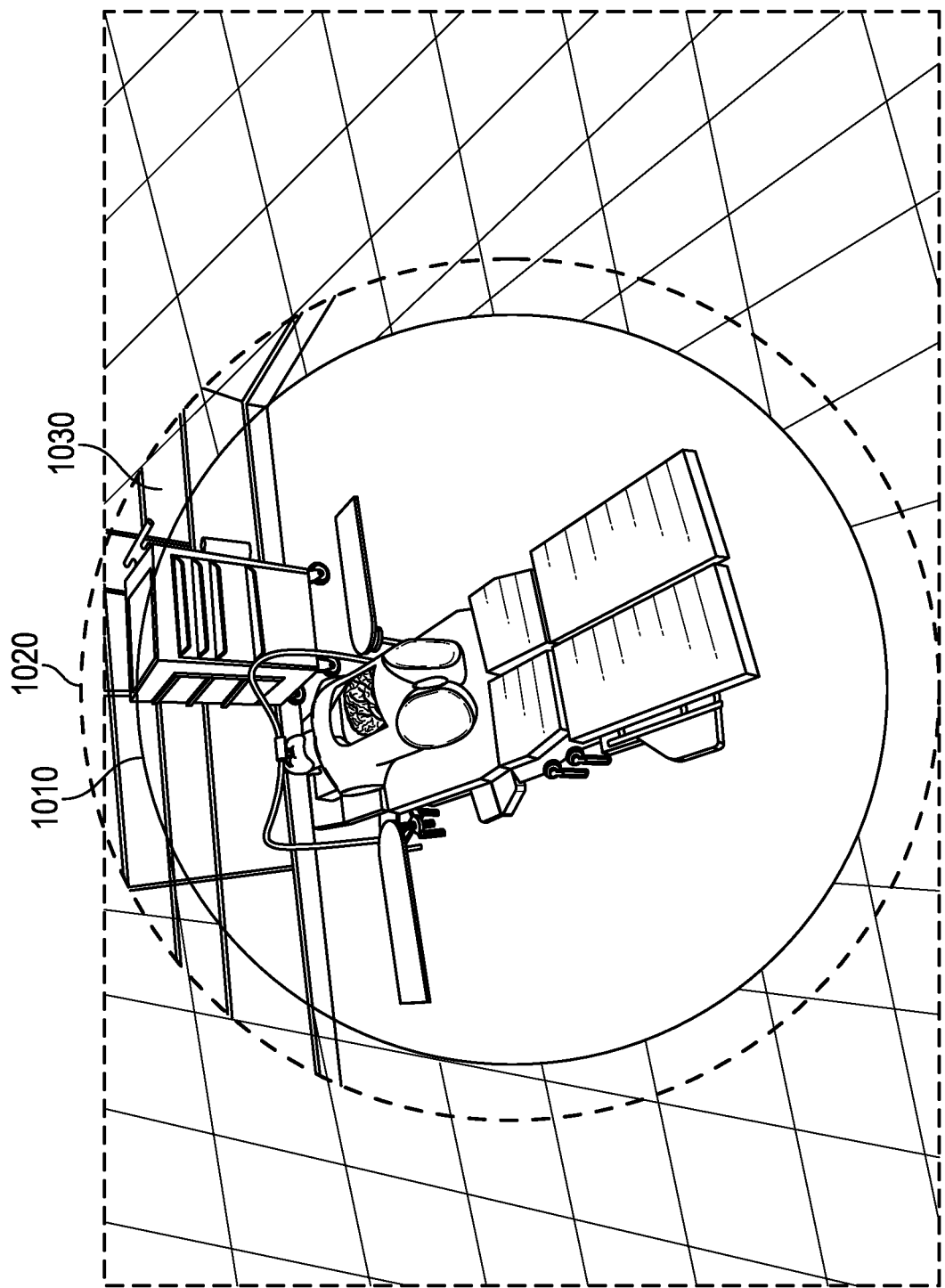
FIG. 10C is a schematic illustration of a transition region for modifying the view of the exemplary virtual robotic surgical environment in flight mode.

As the user freely navigates the virtual environment in flight mode, the displayed view may include features to reduce eye fatigue, nausea, etc. For example, in some variations, the system may include a "comfort mode" in which outer regions of the displayed view are removed as the user navigates in flight mode, which may, for example, help reduce motion sickness for the user. As shown in FIG. 10C, when in the comfort mode, the system may define a transition region 1030 between an inner transition boundary 1010 and an outer transition boundary 1020 around a focal area (e.g., center) of the user's view. Inside the transition region (inside the inner transition boundary 1010), a normal view of the virtual robotic surgical environment is displayed. Outside the transition region (outside the outer transition boundary 1020), a neutral view or plain background (e.g., a plain, gray background) is displayed. Within the transition region 1030, the displayed view may have a gradient that gradually transitions the view of the virtual environment to the neutral view. Although the transition region 1030 shown in FIG. 10C is depicted as generally circular, with generally circular inner and outer transition boundaries 1010 and 1020, in other variations the inner and outer transition boundaries 1010 and 1020 may define a transition region 1030 that is elliptical or other suitable shape. Furthermore, in some variations, various parameters of the transition region, such as size, shape, gradient, etc. may be adjustable by the user and/or set by the system by default.

Figure 11:
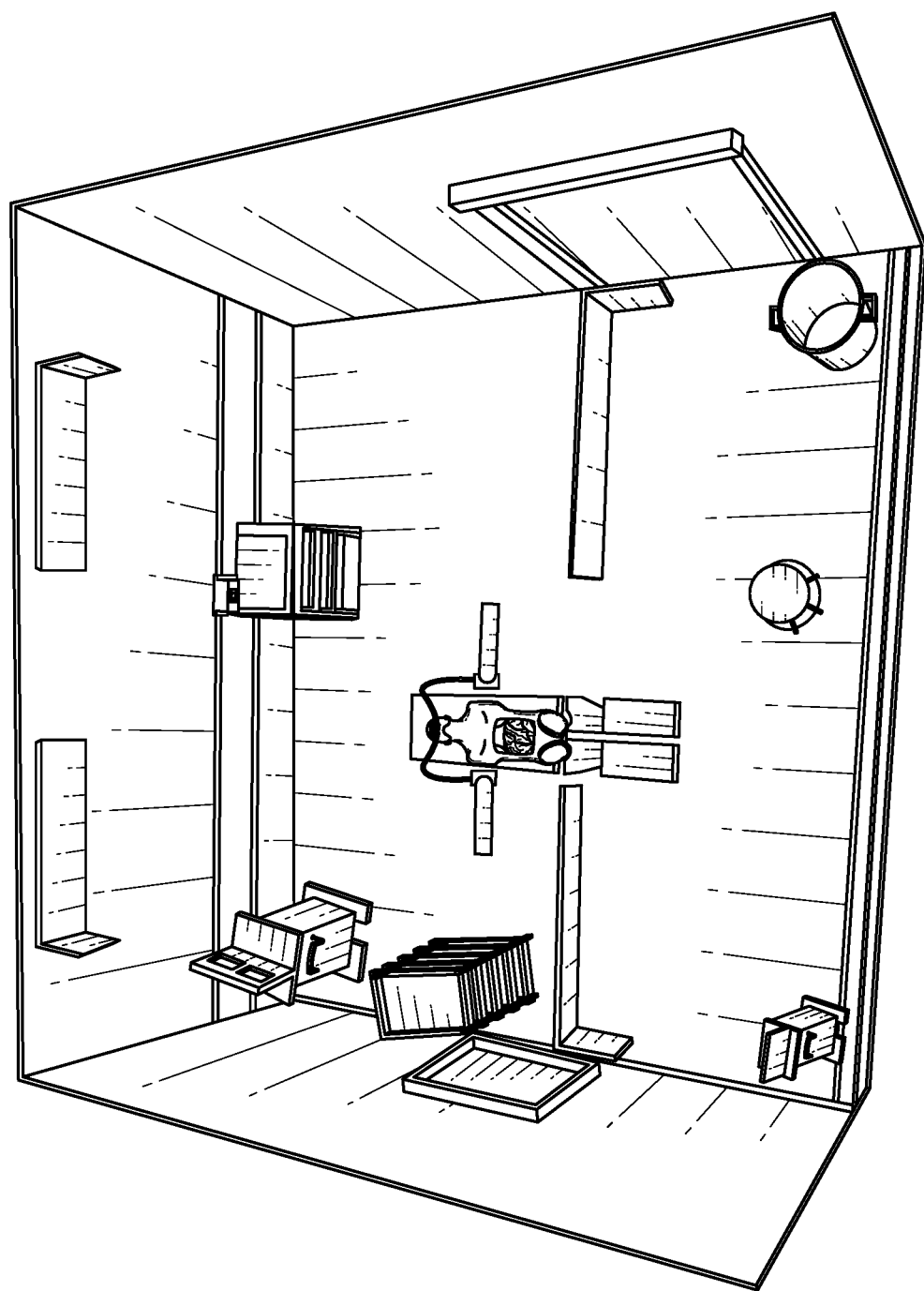
FIG. 11 is a schematic illustration of a virtual robotic surgical environment viewed from a vantage point providing an exemplary dollhouse view of a virtual operating room.

In some variations, as shown in FIG. 11, the user may view the virtual robotic surgical environment from a dollhouse view that allows the user to view the virtual operating room from an overhead vantage point, with a top-down perspective. In the dollhouse view, the virtual operating room may be displayed at a smaller scale factor (e.g., smaller than life-size) on the display, thereby changing the scale of the user relative to the virtual operating room. The dollhouse view may provide the user with additional contextual awareness of the virtual environment, as the user may view the entire virtual operating room at once, as well as the arrangement of its contents, such as virtual equipment, virtual personnel, virtual patient, etc. Through the dollhouse view, for example, the user may rearrange virtual objects in the virtual operating room with fuller contextual awareness. The dollhouse view may, in some variations, be linked in a trajectory along with portals and/or snap points described above.

Environment View Rotation

In some variations, the system may include a user mode that enables the user to navigate the virtual robotic surgical environment by moving the virtual environment around his or her current vantage point. The environment view rotation mode may offer a different manner in which the user may navigate the virtual environment, such as by "grasping" and manipulating the environment as if it were an object. As the user navigates through the virtual environment in such a manner, a "comfort mode" similar to that described above may additionally be implemented to help reduce simulation-related motion sickness. For example, in an environment view rotation mode, the user may rotate a displayed scene around a current vantage point by selecting and dragging the view of the virtual environment around the user's current vantage point. In other words, in the environment view rotation mode, the user's apparent location in the virtual environment appears fixed while the virtual environment may be moved. This is in contrast to other modes, such as, for example, flight mode described above, in which generally the environment may appear fixed while the user moves. Similar to the scaling factor adjustments described above for flight mode, in the environment view rotation mode, the scaling factor of the displayed view of the environment may be controlled by the handheld controllers and/or voice commands (e.g., by using the handheld controllers to select and pull apart two points in the displayed view to zoom in, etc.).

Figure 15:
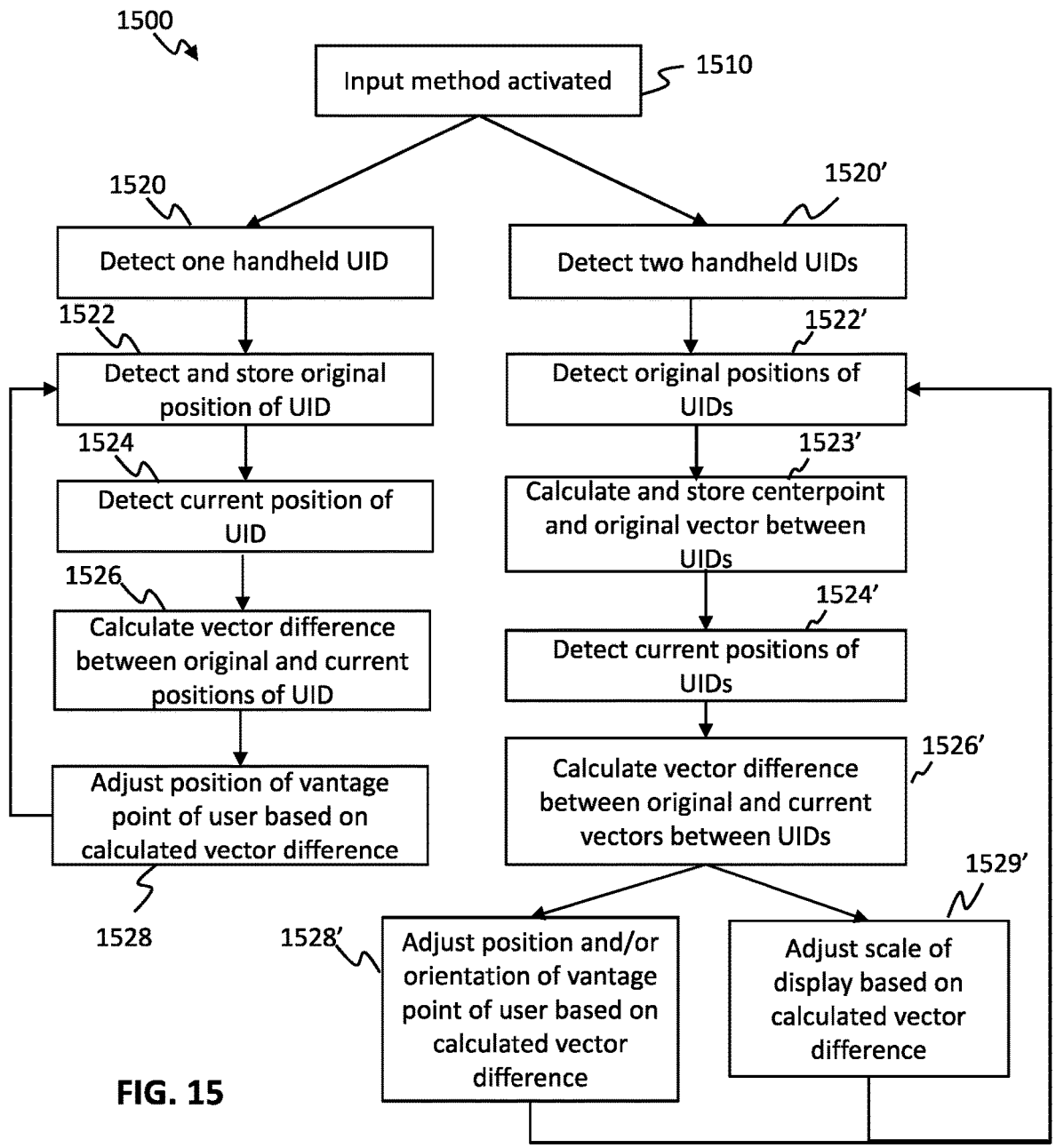
FIG. 15 is a flowchart of an exemplary variation of a method for operating in an environment view rotation mode in a virtual reality system.

For example, as shown in FIG. 15, in one exemplary variation of a method 1500 for operating in an environment view rotation mode, the user may activate a user input method (1510) such as on a handheld controller (e.g., a button or trigger or another suitable feature) or any suitable device. In some variations, one handheld controller (1520) may be detected upon activation of the user input method. The original position of the handheld controller at the time of activation may be detected and stored (1522). Thereafter, as the user moves the handheld controller (e.g., while continuing to activate the user input method), the current position of the handheld controller may be detected (1524). A vector difference between the original (or previous) position and the current position of the handheld controller may be calculated (1526), and position of the vantage point of the user may be adjusted (1528) based at least partially on the calculated vector difference, thereby creating an effect that makes the user feel they are "grabbing" and dragging the virtual environment around.

In some variations, two handheld controllers (1520') may be detected upon activation of the user input method. The original positions of the handheld controllers may be detected (1522'), and a centerpoint and an original vector between the original positions of the handheld controllers (1523') may be calculated and stored. Thereafter, as the user moves one or more both handheld controllers (e.g., while continuing to activate the user input method), the current positions of the handheld controllers may be detected (1524') and used to form the basis for a calculated vector difference between original and current vectors between handheld controllers (1528'). The position and/or orientation of the vantage point of the user may be adjusted (1528'), based on the calculated vector difference. For example, the orientation or rotation of the displayed view may be rotated around the centerpoint between the handheld controller locations, thereby creating an effect that makes the user feel they are "grabbing" and dragging the environment around. Similarly, the scale of the display of the virtual environment (1529') may be adjusted based on the calculated difference in distance between the two handheld controllers, thereby creating an effect that makes the user feel they are "grabbing" and zooming in and out of the displayed view of the virtual environment.

Although the above-described user modes are described separately, it should be understood that aspects of these modes characterize exemplary ways that a user may navigate the virtual robotic surgical environment, and may be combined in a single user mode. Furthermore, some of these aspects may be seamlessly linked. For example, an overhead vantage point generally associated with flight mode may be sequentially linked with one or more portals in a trajectory. Even further, in some variations, a vantage point or displayed view of the virtual environment (e.g., as adjusted via one or more of the above user modes) may be linked to at least one default vantage point (e.g., default in position, orientation, and/or scale). For example, by activating a user input (e.g., on a handheld controller, foot pedal, etc.), a user may "reset" the current vantage point to a designated or predetermined vantage point in the virtual environment. The user's current vantage point may, for example, be gradually and smoothly animated in order to transition to default values of position, orientation, and/or scale.

Supplemental Views

Figure 12:
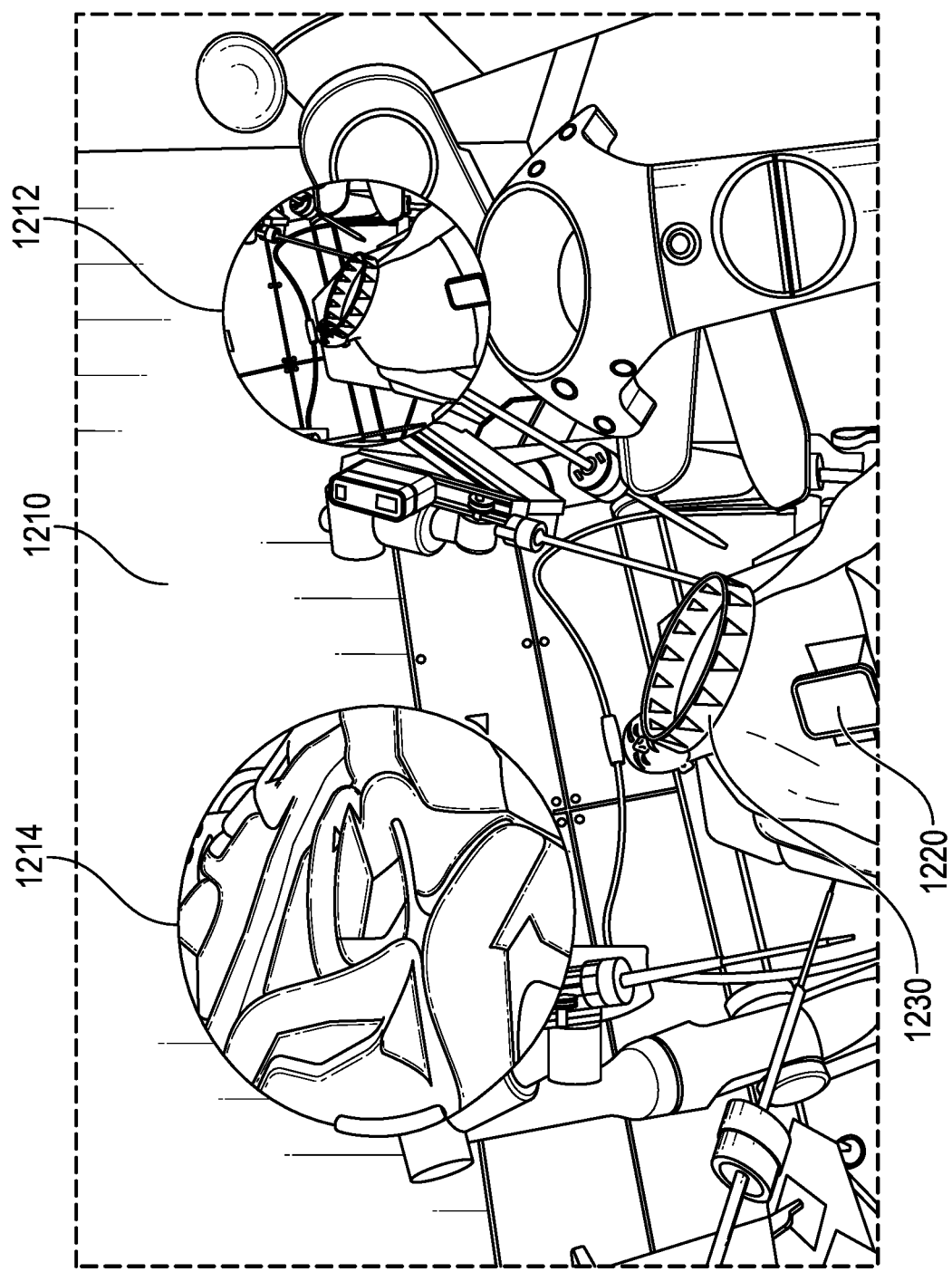
FIG. 12 is a schematic illustration of a view of a virtual robotic surgical environment with an exemplary heads-up display for displaying supplemental views.

In some variations, an exemplary user mode or modes of the system may display one or more supplemental views of additional information to a user, such as overlaid over or inset in the primary, first-person perspective view of the virtual robotic surgical environment. For example, as shown in FIG. 12, a heads-up display 1210 (HUD) may provide a transparent overlay over a primary first-person perspective view of the virtual environment. The HUD 1210 may be toggled on and off, thereby allowing the user to control whether to display the HUD 1210 at any particular time. Supplemental views of additional information, such as that described below, may be placed onto the HUD such that the user may observe the supplemental views without looking away from the primary view. For example, the supplemental views may "stick" to the HUD 1210 and move with the user's head movement such that the supplemental views are always in the user's field of view. As another example, supplemental views of additional information may be loosely fixed to the HUD 1210, in that the supplemental views may be small or at least partially hidden off-screen or in peripheral vision when the user's head is generally facing forward, but minor or slight head movement to one side may expand and/or bring one or more supplemental views into the user's field of view. The one or more supplemental views may be arranged on the HUD 1210 in a row, grid, or other suitable arrangement. In some variations, the HUD 1210 may include predetermined "snap" points to which the supplemental views (e.g., camera views, etc.) are positioned. For example, the user may select a supplemental view on the HUD 1210 for closer inspection, then replace the supplemental view on the HUD 1210 by dragging it generally in the direction of a snap point, whereupon the supplemental view may be drawn to and fixed at the snap point without needing to be precisely placed there by the user.

Figure 13:
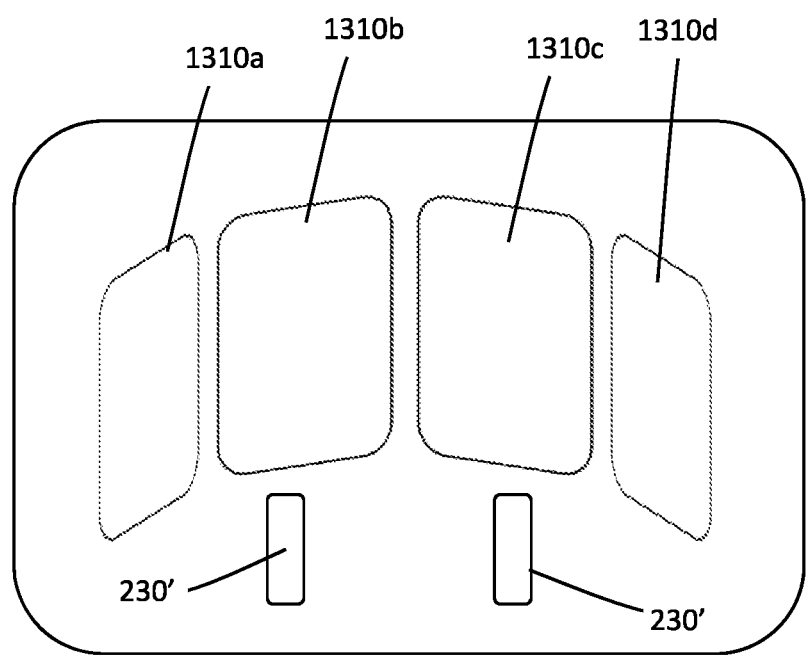
FIG. 13 is a schematic illustration of a display provided by one variation of a virtual reality system operating in a virtual command station mode.

As another example, in a virtual command station mode, one or more supplemental views may be displayed in a virtual space with one or more content windows or panels arranged in front of the user in the virtual space (e.g., similar to a navigable menu). For example, as shown in FIG. 13, multiple content windows (e.g., 1310*a*, 1310*b*, 1310*c*, and 1310*d*) may be positioned in a semi-circular arrangement or other suitable arrangement for display to a user. The arrangement of the content windows may be adjusted by the user (e.g., using handheld controllers with their graphical representations 230' to select and drag or rotate content windows). The content windows may display, for example, an endoscope video feed, a portal view, a "stadium" overhead view of the virtual operating room, patient data (e.g., imaging), other camera or patient information views such as those described herein, etc. By viewing multiple panels simultaneously, the user may be able to simultaneously monitor multiple aspects of the virtual operating room and/or with the patient, thereby allowing the user to have an overarching and broader awareness of the virtual environment. For example, the user may become aware of and then respond more quickly to any adverse events in the virtual environment (e.g., simulated negative reactions of the virtual patient during a simulated surgical procedure).

Furthermore, the virtual command station mode may enable a user to select any one of the content windows and become immersed in the displayed content (e.g., with a first-person perspective). Such a fully immersive mode may temporarily dismiss the other content windows, or may minimize (e.g., be relegated to a HUD overlaid over the selected immersive content). As an illustrative example, in the virtual command station mode, the system may display multiple content windows including an endoscopic camera video feed showing the inside of a virtual patient's abdomen. The user may select the endoscopic camera video feed to become fully immersed in the virtual patient's abdomen (e.g., while still manipulating robotic arms and instruments attached to the arms).

Camera Views

In some variations, a user mode may enable the user to place a virtual camera in a selected vantage point in the virtual environment, and a window view of the virtual environment from the selected vantage point may be displayed in the HUD such that the user may simultaneously view both his first-person perspective field of view and the camera view (the view provided by the virtual camera) that may update in real time. A virtual camera may be placed in any suitable location in the virtual environment (e.g., inside or outside the patient, overhead the patient, overhead the virtual operating room, etc.). For example, as shown in FIG. 12, the user may place a virtual camera 1220 (e.g., using object gripping as described above) near the pelvic region of a virtual patient and facing the patient's abdomen so as to provide a "virtual video feed" of the patient's abdomen. Once placed, a virtual camera 1220 may be subsequently repositioned. A camera view (e.g., a circular inset view, or window of any suitable shape) may be placed on the HUD as a window view showing the virtual video feed from the vantage point of the virtual camera 1220. Similarly, multiple virtual cameras may be placed in the virtual environment to enable multiple camera views to be shown on the HUD. In some variations, a predetermined arrangement of one or more virtual cameras may be loaded, such as part of a configuration file for the virtual reality processor to incorporate into the virtual environment.

In some variations, the system may offer a range of different kinds of virtual cameras, which may provide different kinds of camera views. One exemplary variation of a virtual camera is a "movie" camera that is configured to provide a live virtual feed of the virtual environment (e.g., movie camera view 1212 in FIG. 12). Another exemplary variation of a virtual camera is an endoscopic camera which is attached to a virtual endoscope to be placed in a virtual patient. In this variation, the user may, for example, virtually perform a technique for introducing the virtual endoscope camera into the virtual patient and subsequently monitor the internal workspace inside the patient by viewing the virtual endoscopic video feed (e.g., endoscopic camera view 1214 in FIG. 12). In another exemplary variation, the virtual camera may be a wide-angle (e.g., 360-degree, panoramic, etc.) camera that is configured to provide a larger field of view of the virtual environment. In this variation, the window camera view may, for example, be displayed as a fish-eye or generally spherical display.

Various aspects of the camera view may be adjusted by the user. For example, the user may adjust the location, size, scale factor, etc. of the camera view (e.g., similar to adjustments of portals as described above). As another example, the user may select one or more filters or other special imaging effects to be applied to the camera view. Exemplary filters include filters that highlight particular anatomical features (e.g., tumors) or tissue characteristics (e.g., perfusion) of the virtual patient. In some variations, one or more virtual cameras may be deselected or "turned off" (e.g., have the virtual camera and/or associated camera view selectively hidden) or deleted, such as if the virtual camera or its associated camera view is obstructing the user's view of the virtual environment behind the virtual camera or camera view.

In some variations, a camera view may function similarly to a portal (described above) to enable the user to navigate quickly around the virtual environment. For example, with reference to FIG. 12, a user may select the camera view 1212 (e.g., highlight or grab and pull the camera view 1212 toward himself) to be transported to the vantage point of the camera view 1212.

Patient Data Views, etc.

In some variations, a user mode may enable display of patient data and other information on the HUD or another suitable location in the display. For example, patient imaging information (e.g., ultrasound, X-ray, MRI, etc.) may be displayed in a supplemental display, overlaid over the patient (e.g., as simulated augmented reality). A user may, for example, view patient images as reference while interacting with the virtual patient. As another example, patient vitals (e.g., heart rate, blood pressure, etc.) may be displayed to the user in a supplemental view.

In another variation, a user mode may enable display of other suitable information, such as training videos (e.g., exemplary surgical procedures recorded from a previous procedure), video feed from a mentor or trainer surgeon, etc. providing guidance to a user.

Virtual Reality System Applications

Generally, the virtual reality system may be used in any suitable scenario in which it is useful to simulate or replicate a robotic surgical environment. In some variations, the virtual reality system may be used for training purposes, such as allowing a surgeon to practice controlling a robotic surgical system and/or to practice performing a particular kind of minimally-invasive surgical procedure using a robotic surgical system. The virtual reality system may enable a user to better understand the movements of the robotic surgical system in response to user commands, both inside and outside the patient. For example, a user may don a head-mounted display under supervision of a mentor or trainer who may view the virtual reality environment alongside the user (e.g., through a second head-mounted display, through an external display, etc.) and guide the user through operations of a virtual robotic surgical system within the virtual reality environment. As another example, a user may don a head-mounted display and may view, as displayed on the immersive display (e.g., in a content window, the HUD, etc.) a training-related video such as a recording of a previously performed surgical procedure.

As another example, the virtual reality system may be used for surgical planning purposes. For example, a user may operate the virtual reality system to plan surgical workflow. Configuration files of virtual objects (e.g., robotic surgical system including arms and tool drivers, user console, end effectors, other equipment, patient bed, patient, personnel, etc.) may be loaded into a virtual robotic surgical environment as representative of actual objects that will be in the actual (i.e., non-virtual, or real) operating room. Within the virtual reality environment, the user may adjust features of the virtual operating room, such as positioning the user console, patient bed, and other equipment relative to one another in a desired arrangement. The user may additionally or alternatively use the virtual reality system to plan aspects of the robotic surgical system, such as selecting number and location of ports for entry of the surgical instruments, or determining optimum number and position/orientation (e.g., mounting location, arm pose, etc.) of robotic arms for a procedure, such as for minimizing potential collisions between system components during the surgical procedure. Such virtual arrangements may be based on, for example, trial-and-error, previous setups for similar surgical procedures and/or similar patients, etc. In some variations, the system may additionally or alternatively propose virtual arrangements selected based on machine learning techniques applied to datasets of previously-performed surgical procedures for various kinds of patients.

As yet another example, the virtual reality system may be used for R&D purposes (e.g., simulation). For example, a method for designing a robotic surgical system may include generating a virtual model of a robotic surgical system, testing the virtual model of the robotic surgical system in a virtual operating room environment, modifying the virtual model of the robotic surgical system based on the testing, and building the robotic surgical system based on the modified virtual model. Aspects of the virtual model of the robotic surgical system that may be tested in the virtual operating room environment include physical characteristics of one or more components of the robotic surgical system (e.g., diameter or length of arm links). For example, a virtual model of a particular design of a robotic arm may be built and implemented in a virtual environment, where the virtual model may be tested with respect to particular arm movements, surgical procedures, etc. (e.g., test for likelihood of collision between the robotic arm and other objects). Accordingly, a design of a robotic arm (or similarly, any other component of the robotic surgical system) may be at least initially tested by testing a virtual implementation of the design, rather than testing a physical prototype, thereby accelerating the R&D cycle and reducing costs.

Other aspects that may be tested include functionality of one or more components of the robotic surgical system (e.g., control modes of a control system). For example, as described above, a virtual operating environment application may pass status information to a kinematics application, and the kinematics application may generate and pass commands based on control algorithms, where the virtual reality processor may use the commands to cause changes in the virtual robotic surgical environment (e.g., move a virtual robotic arm in a particular way in accordance with relevant control algorithms). As such, software control algorithms may be embodied in a virtual robotic system for testing, refinement, etc. without requiring a physical prototype of the relevant robotic component, thereby conserving R&D resources and accelerating the R&D cycle.

In another example, the virtual reality system may be used to enable multiple surgeons to collaborate in the same virtual reality environment. For example, multiple users may don head-mounted displays and interact with each other (and with the same virtual robotic system, the same virtual patient, etc.) in the virtual reality environment. The users may be physically in the same room or general location, or may be remote from one another. For example, one user may be tele-mentoring the other as they collaborate to perform a surgical procedure on the virtual patient.

Specific illustrative exemplary applications of the virtual reality system are described in further detail below. However, it should be understood that applications of the virtual reality system are not limited to these examples and general application scenarios described herein.

Example 1—Over the Bed

A user may use the virtual reality system to simulate an over-the-bed scenario in which he is adjacent to a patient bed or table and operating both a robotic surgical system and a manual laparoscopic tool. Such simulation may be useful for training, surgical planning, etc. For example, the user may staple tissue in a target segment of a virtual patient's intestine using both a virtual robotic tool and a virtual manual tool.

In this example, the user dons a head-mounted display providing an immersive view of a virtual reality environment, and may use handheld controllers to navigate within the virtual reality environment to be adjacent to a virtual patient table on which a virtual patient lies. A proximal end of a virtual robotic arm is attached to the virtual patient table, and a distal end of the virtual robotic arm supports a virtual tool driver actuating virtual forceps that are positioned within the abdomen of the virtual patient. A virtual manual laparoscopic stapler tool is passed through a virtual cannula and having a distal end positioned within the abdomen of the virtual patient. Additionally, an endoscopic camera is positioned within the abdomen of the virtual patient, and provides a virtual camera feed showing the surgical workspace within the abdomen of the virtual patient (including patient tissue, virtual robotically-controlled forceps, and a virtual manual laparoscopic stapler tool).

The user continues to view the virtual environment through the immersive display in the head-mounted display, as well as the virtual endoscopic camera feed displayed in a window view in a heads-up display overlaid in the user's field of view. The user holds in one hand a handheld controller that is configured to control the robotically-driven virtual forceps. The user holds in another hand a laparoscopic hand controller that is configured to control the virtual manual laparoscopic stapler tool, with the laparoscopic hand controller passing through a cannula mounted in a mock patient body made of foam. The laparoscopic hand controller is calibrated to correspond to the virtual manual laparoscopic stapler tool. The user manipulates the handheld controller to operate the robotically-controlled forceps to manipulate the intestine of the virtual patient and uncover a target segment of the intestine. With the target segment of the intestine exposed and accessible, the user manipulates the laparoscopic hand controller to apply virtual staples to the target segment via the virtual manual laparoscopic stapler tool.

Example 2—Collision Resolution from User Console

When using the virtual reality system, a user may desire to resolve collisions between virtual components of the virtual robotic surgical system, even though the user may not be adjacent the colliding virtual components (e.g., the user may be seated at a distance away from the virtual patient table, such as at a virtual user console). In this example, the user dons a head-mounted display providing an immersive view provided by a virtual endoscope placed inside an abdomen of a virtual patient. Proximal ends of two virtual robotic arms are attached to separate locations on a virtual patient table, on which the virtual patient lies. Distal ends of the virtual robotic arms support respective tool drivers actuating virtual forceps that are positioned within the abdomen of the virtual patient. The user manipulates the handheld controllers to operate the two robotically-controlled virtual forceps, which manipulate virtual tissue within the virtual patient. This movement may cause a collision involving at least one of the virtual robotic arms (e.g., a virtual robotic arm may be posed so as to create a collision with itself, the virtual robotic arms may be posed so as to create a collision with each other, a virtual robotic arm may be posed so as to create a collision with the patient or nearby obstacle, etc.).

The virtual reality system detects the collision based on status information of the virtual robotic arms, and alerts the user regarding the collision. The system displays an overhead or other suitable view from a suitable vantage point of the virtual robotic surgical system, such as in a window view (e.g., picture-in-picture view). The location of the collision is highlighted in the displayed window view, such as by outlining the affected colliding components with red or another contrasting color. Alternatively, the user may detect the collision himself by monitoring a camera video feed from a virtual camera placed overhead the virtual patient table.

Upon becoming aware of the collision, the user may zoom out or adjust the scale of his immersive view of the virtual reality environment. The user may engage an arm repositioning control mode that locks the position and orientation of the virtual forceps within the patient. Using the handheld controllers in an object gripping user mode, the user may grab onto virtual touchpoints on the virtual robotic arms and reposition (repose) the virtual robotic arms so as to resolve the collision while the control mode maintains the position and orientation of the virtual forceps during the arm repositioning. Once the virtual robotic arms are repositioned such that the collision is resolved, the user may zoom back into the previous vantage point, disengage the arm repositioning control mode, and resume using the handheld controllers to operate the virtual forceps within the virtual patient.

Example 3—Coordinated Relocation of Multiple Surgical Instruments from User Console When using the virtual reality system, a user may find it useful to stay substantially in an endoscopic view and relocating multiple virtual surgical instruments (e.g., end effectors, cameras) as a group rather than individually within the virtual patient, thereby saving time, as well as making it easier for the user to maintain contextual awareness of the instruments relative to the virtual patient's anatomy. In this example, the user dons a head-mounted display providing an immersive view provided by a virtual endoscope placed inside an abdomen of a virtual patient. Proximal ends of two virtual robotic arms are attached to separate locations on a virtual patient table, on which the virtual patient lies. Distal ends of the virtual robotic arm support respective tool drivers actuating virtual forceps that are positioned in the pelvic area of the virtual patient. The user may manipulate handheld controllers to operate the virtual forceps.

The user may wish to move the virtual endoscope and the virtual forceps to another target region of the virtual patient's abdomen, such as the spleen. Rather than move each surgical instrument individually, the user may engage a coordinated relocation mode. Once this mode is engaged, the endoscopic camera view zooms out along the axis of the endoscope to a distance sufficient to allow the user to view the new target region (spleen). A spherical indicator is displayed at the distal end of the endoscope that encapsulates the distal end of the virtual endoscope and the distal ends of the virtual forceps. The user manipulates at least one handheld controller to withdraw the virtual endoscope and the virtual forceps away from the surgical workspace (e.g., until the user can see the distal end of the virtual cannula in the virtual endoscopic view), then grab and move the spherical indicator from the pelvic area to the spleen. Once the user finalizes the new target region by moving the spherical indicator to the new target region, the virtual endoscope and virtual forceps automatically travel to the new target region and the virtual endoscopic camera view zooms to show the new target region. Throughout this relatively large-scale move, the user views the virtual environment with substantially an endoscopic view of the virtual environment, thereby enabling the user to maintain awareness of the virtual patient's anatomy instead of transferring his focus between instrument and anatomy.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method for collaboration of users in a virtual surgical environment, comprising:
   rendering, to a first display of a first user, a virtual surgical environment from a first vantage point, and to a second display of a second user, the virtual surgical environment from a second vantage point, wherein the virtual surgical environment includes a virtual operating room, a virtual patient table, a virtual patient on the virtual patient table, and a virtual robotic arm to enable the first user to tele-mentor the second user to perform a surgical procedure on the virtual patient, wherein a distal end of the virtual robotic arm supports a virtual tool driver to actuate a virtual tool within an abdomen of the virtual patient;
   generating, in response to user input from at least one of the first user or the second user, a motion of the virtual robotic arm with the virtual tool driver and the virtual tool in the virtual surgical environment; and
   rendering the motion of the virtual robotic arm to the first display from the first vantage point and to the second display from the second vantage point to enable collaboration between the first user and the second user.

2. The method of claim 1, wherein the virtual surgical environment enables the first user to tele-mentor the second user while the first user and the second user are remote from one another.

3. The method of claim 1, further comprising:
rendering, to the first display and the second display, patient data overlaying a virtual patient as simulated augmented reality.

4. The method of claim 1, further comprising:
rendering, to the first display and the second display, patient data comprising at least one of an ultrasound, X-ray, or MRI.

5. The method of claim 1, further comprising:
rendering, to the first display and the second display, patient images of the virtual patient as the first user interacts with the virtual patient in the virtual surgical environment.

6. The method of claim 1, wherein the virtual surgical environment enables the first user to change from the first vantage point to another vantage point.

7. The method of claim 1, further comprising:
rendering, to the first display and the second display, the virtual surgical environment from a third vantage point of a virtual camera.

8. The method of claim 1, further comprising:
rendering a first portal in a first-person view to the first display and a second portal in a first-person view to the second display.

9. The method of claim 1, further comprising:
generating a first trajectory between a first portal and a second portal rendered to the first display and a second trajectory between a third portal and a fourth portal rendered to the second display.

10. The method of claim 1, wherein the virtual surgical environment enables the first user and the second user to interact with one other.

11. The method of claim 1, wherein the virtual surgical environment enables the first user to take control from the second user during the surgical procedure.

12. A virtual reality system for collaboration of users in a virtual surgical environment, the virtual reality system having one or more processors configured to:
render, to a first display of a first user, a virtual surgical environment from a first vantage point, and to a second display of a second user, the virtual surgical environment from a second vantage point, wherein the virtual surgical environment includes a virtual operating room, a virtual patient table, a virtual patient on the virtual patient table, and a virtual robotic arm to enable the first user to tele-mentor the second user to perform a surgical procedure on the virtual patient, wherein a distal end of the virtual robotic arm supports a virtual tool driver to actuate a virtual tool within an abdomen of the virtual patient;
generate, in response to user input from at least one of the first user or the second user, a motion of the virtual robotic arm with the virtual tool driver and the virtual tool in the virtual surgical environment; and
render the motion of the virtual robotic arm to the first display from the first vantage point and to the second display from the second vantage point to enable collaboration between the first user and the second user.

13. The virtual reality system of claim 12, wherein the virtual surgical environment enables the first user to tele-mentor the second user from a remote location in a different building, city, or country.

14. The virtual reality system of claim 12, wherein the one or more processors configured to render, to the first display and the second display, patient imaging information in a supplemental display overlaying the virtual patient.

15. The virtual reality system of claim 12, wherein the one or more processors configured to render, to the first display and the second display, patient vitals including at least one of a heartrate, a temperature, or a blood pressure.

16. The virtual reality system of claim 12, wherein the one or more processors configured to render, to the first display and the second display, patient images of the virtual patient as the first user interacts with the virtual patient in the virtual surgical environment.

17. The virtual reality system of claim 12, wherein the virtual surgical environment enables the first user and the second user to adjust their first vantage points.

18. A non-transitory computer readable medium storing instructions operable to cause one or more processors to perform operations comprising:
rendering, to a first display of a first user, a virtual surgical environment from a first vantage point, and to a second display of a second user, the virtual surgical environment from a second vantage point, wherein the virtual surgical environment includes a virtual operating room, a virtual patient table, a virtual patient on the virtual patient table, and a virtual robotic arm to enable the first user to tele-mentor the second user to perform a surgical procedure on the virtual patient, wherein a distal end of the virtual robotic arm supports a virtual tool driver to actuate a virtual tool within an abdomen of the virtual patient;
generating, in response to user input from at least one of the first user or the second user, a motion of the virtual robotic arm with the virtual tool driver and the virtual tool in the virtual surgical environment; and
rendering the motion of the virtual robotic arm to the first display from the first vantage point and to the second display from the second vantage point to enable collaboration between the first user and the second user.

19. The non-transitory computer readable medium storing instructions of claim 18, the operations further comprising:
deselecting a virtual camera to turn off a third vantage point of the virtual camera.

20. The non-transitory computer readable medium storing instructions of claim 18, wherein the first vantage point and the second vantage point each correspond to a portal that serves as a transportation gateway in the virtual surgical environment.

* * * * *